US008329661B2

(12) United States Patent
Christa et al.

(10) Patent No.: US 8,329,661 B2
(45) Date of Patent: Dec. 11, 2012

(54) METHOD FOR USING HIP/PAP POLYPEPTIDE COMPOSITION FOR LIVER REGENERATION AND PREVENTION OF LIVER FAILURE

(75) Inventors: Laurence Christa, Bourg la Reine (FR); Christian Brechot, Paris (FR); Marie-Thérèse Simon-Gage-Soufflot, Chaville (FR); Alain Pauloin, Voisin-le-Bretonneux (FR); J. Guilherme Tralhao, Coimbra (PT)

(73) Assignees: Instiut National de la Santéet de la Recherche Médicale (INSERM), Paris (FR); Universite Rene Descartes, Paris (FR)

( * ) Notice: Subject to any disclaimer, the term of this patent is extended or adjusted under 35 U.S.C. 154(b) by 0 days.

(21) Appl. No.: 13/032,521

(22) Filed: Feb. 22, 2011

(65) Prior Publication Data
US 2011/0144036 A1    Jun. 16, 2011

Related U.S. Application Data

(62) Division of application No. 10/561,034, filed as application No. PCT/EP2004/006633 on Jun. 18, 2004, now abandoned.

(30) Foreign Application Priority Data

Jun. 18, 2003  (EP) .................................... 03291487

(51) Int. Cl.
*A61P 1/16*     (2006.01)
*A61K 38/17*    (2006.01)
*C07K 14/47*    (2006.01)

(52) U.S. Cl. ....... 514/21.2; 514/838; 514/893; 514/894; 530/350; 530/846

(58) Field of Classification Search .......................... None
See application file for complete search history.

(56) References Cited

U.S. PATENT DOCUMENTS 5,834,214 A * 11/1998 Iovanna et al. ................ 435/7.9
2011/0144036 A1 * 6/2011 Christa et al. ................ 514/21.2

FOREIGN PATENT DOCUMENTS
WO    WO 91/16428    10/1991

OTHER PUBLICATIONS

Moniaux et al, 2011. Hepatology. 53:618-627.*
Kandil et al, (May 17-22, 2003). Digestive Disease Week Abstracts and Itinerary Planner, Abstract No. 738, 1 page as printed.*
"Evaluation Report, Research Unit: Physiopathogenesis and treatment of fulminant hepatitis and liver cancer," *French Research and Education Evaluation Agency (AERES)*, 11 pages, Dec. 2008.

"Guidance for industry—For the submission of chemistry, manufacturing, and controls information for a therapeutic recombinant DNA-derived product or a monoclonal antibody product for in vivo use," *Center for Biologics Evaluation and Research (CBER) and Center for Drug Evaluation and Research (CDER)*, Aug. 1996.
"Guidance for industry—Q6B specifications: test procedures and acceptance criteria for biotechnological/biological products," *U.S. Department of Health and Human Services, Food and Drug Administration, Center for Drug Evaluation and Research (CDER), and Center for Biologics Evaluation and Research (CBER)*, pp. 1-21, Aug. 1999.
"Guideline for industry—Quality of biotechnological products: stability testing of biotechnological/biological products," *Expert Working Group (Quality) of the International Conference on Harmonisation of Technical Requirements for Registration of Pharmaceuticals for Human Use (ICH)*, pp. 1-10, Jul. 1996.
"Points to consider in the production and testing of new drugs and biologicals produced by recombinant DNA technology," *Office of Biologics Research and Review—Center for Drugs and Biologics*, Draft, Apr. 10, 1985.
"Production and quality control of medicinal products derived by recombinant DNA technology," *European Agency for the Evaluation of Medicinal Products (EMEA)*, pp. 205-216, Dec. 1994.
"Quality of biotechnological products: stability testing of biotechnological/biological products," *European Agency for the Evaluation of Medicinal Products (EMEA)*, pp. 263-273, Dec. 1995.
"Use of transgenic animals in the manufacture of biological medicinal products for human use," *European Agency for the Evaluation of Medicinal Products (EMEA)*, pp. 287-294, Dec. 1994.
Bork, "Powers and Pitfalls in Sequence Analysis: The 70% Hurdle," *Genome Research*, 10(4):398, 2000.
Brenner, "Errors in genome annotation," *Trends in Genetics*, 15(4):132, 1999.
Cervello et al., "Expression of HIP/PAP mRNA in human hepatoma cell lines," *Ann. Ny. Acad. Sci.*, 963:53-58, 2002.
Christa et al., Hepatocarcinoma-intestine-pancreas/pancreatic associated protein (HIP/PAP) is expressed and secreted by proliferating ducules as well as by hepatocarcinoma and cholangiocarcinoma cells. *Am J Pathol*, 155:1525-1533, 1999.
Christa et al., "High expression of the human hepatocarcinoma-intestine-pancreas/pancreatic-associated protein (HIP/PAP) gene in the mammary gland of lactating transgenic mice—Secretion into the milk and purification of the HIP/PAP lectin," *Eur. J. Biochem.*, 267:1665-1671, 2000.

(Continued)

*Primary Examiner* — Zachary Howard
(74) *Attorney, Agent, or Firm* — Fulbright & Jaworski L.L.P.

(57) ABSTRACT

This invention is based on the experimental finding that HIP/PAP has mitogenic and antiapoptotic effects in vitro on hepatocytes in primary culture. Moreover, HIP/PAP is a mitogenic and anti-apoptotic molecule for hepatocytes, in vivo, during liver failure and liver regeneration. The present invention is also based on the experimental finding that HIP/PAP administration has no adverse effects in mammals. This invention concerns a pharmaceutical composition for stimulating liver regeneration in vivo including after chronic/acute liver failure, comprising an effective amount of a polypeptide comprising an amino acid sequence having 90% amino acid identity with the polypeptide consisting of the amino acid sequence starting at the amino acid residue (36) and ending at the amino acid residue (175) of sequence SEQ ID No 1, in combination with at least one physiologically acceptable excipient.

20 Claims, 13 Drawing Sheets

OTHER PUBLICATIONS

Christa et al., "HIP/PAP is an adhesive protein expressed in hepatocarcinoma, normal Paneth, and pancreatic cells," *Am. J. Physiol.*, 271:G993-G1002, 1996.

Doerks et al., "Protein annotation: detective work for function prediction ," *Trends in Genetics*, 14(6):248, 1998.

Kaufman et al., "Transgenic Analysis of a 100-kb Human beta-Globin Cluster-Containing DNA Fragment Propagated as a Bacterial Artificial Chromosome," Blood, 94:3178-3184, 1999.

Lasserre et al., "A novel gene (HIP) activated in human primary liver cancer", *Cancer Res.*, 52:5089-5095, 1992.

Ngo et al., "Computational Complexity Protein Structure Prediction, and the Levinthal Paradox ,"In: *The protein folding problem and tertiary structure prediction*," Chapter 14, ," Eds. Kenneth M. Merz and Scott M. Le Grand, Boston : Birkhäuser , pp. 433-440 and 492-495 only, 1994.

Office Communication, issued in U.S. Appl. No. 10/561,034, dated Sep. 9, 2009.

Office Communication, issued in U.S. Appl. No. 10/561,034, dated Feb. 18, 2010.

Office Communication, issued in U.S. Appl. No. 10/561,034, dated Oct. 26, 2010.

Philipps, "The challenge of gene therapy and DNA delivery," *J. Pharm. Pharmacology*, 53:1169-1174, 2001.

Simon Marie-Therese et al., "HIP/PAP stimulates liver regeneration after partial hepatectomy and combines mitogenic and anti-apoptotic functions through the PKA signaling pathway", *Faseb Journal*, 17:1441-1450, 2003.

Stolnick et al., "From genes to protein structure and function: novel applications of computational approaches in the genomic era ," *Trends in Biotech.*, 18(1):34-39, 2000.

Tanaka et al., "Biological effects of human insulin receptor substrate-1 overexpression in hepatocytes," *Hepatology*, 26(3):598-604, 1997.

Wang et al., "Rapid analysis of gene expression (RAGE) facilitates universal expression profiling," *Nucl. Acids Res.*, 27:4609-4618, 1999.

Wells, "Additivity of mutational effects in proteins," *Biochemistry*, 29(37):8509-8517, 1990.

Abergel et al., "Crystallization and preliminary crystallographic study of HIP/PAP, a human C-lectin overexpressed in primary liver cancers," *Acta Crystallogr. D. Biol. Crystallogr.*, 55:1487-1489, 1999.

Hussaini and Farrington, "Idiosyncratic drug-induced liver injury: an overview," *Expert Opin. Drug Saf.*, 6:673-684, 2007.

Iovanna and Dagorn, "The multifunctional family of secreted proteins containing a C-type lectin-like domain linked to a short N-terminal peptide," *Biochem. Biophys. Acta.*, 1723:8-18, 2005.

Klaunig et al., "Mouse liver cell culture. I. Hepatocyte isolation," In Vitro, 17:913-925, 1981.

Manzo et al., "TNF-related apoptosis-inducing ligand: Signaling of a 'smart' molecule," *Int. J. Blochem. Cell Biol.*, 41(3):460-466, 2009. Available online Dec. 28, 2007.

Renton et at., "Effects of polyribonoinosinic acid polyribocytidylic acid and a mouse interferon preparation on cytochrome P-450-dependent monoxygenase systems in cultures of primary mouse hepatocytes," *Mol. Pharmacol.*, 14(4):672-681, 1978.

Schiesser et al., "Conformational changes of pancreatitis-associated protein (PAP) activated by trypsin lead to insoluble protein aggregates," *Pancreas*, 22:186-192, 2001.

\* cited by examiner

METHOD FOR USING HIP/PAP POLYPEPTIDE COMPOSITION FOR LIVER REGENERATION AND PREVENTION OF LIVER FAILURE

This application is a divisional application of co-pending U.S. application Ser. No. 10/561,034 filed 24 Jul. 2006, which is a national phase application under 35 U.S.C. §371 of International Application No. PCT/EP2004/006633 filed 18 Jun. 2004, which claims priority to European Application No. 03291487.1 filed 18 Jun. 2003. The entire text of each of the above-referenced disclosures is specifically incorporated herein by reference without disclaimer.

FIELD OF THE INVENTION

The present invention concerns the use of the human hepatocarcinoma-intestine-pancreas/pancreatic-associated protein (HIP/PAP) for stimulating liver regeneration and also for the prevention of liver failure.

BACKGROUND ART

Liver failure occurs in a number of acute and chronic clinical conditions, including drug-induced hepatotoxicity, viral infections, vascular injury, autoimmune disease, or blunts trauma. In addition, patients subject to inborn errors of metabolism may be at risk for developing liver failure. Symptoms of liver failure occurring as a result of these clinical conditions include, for example, fulminant acute hepatitis, chronic hepatitis, or cirrhosis, and in many instances, the restoration of normal liver function is vital to the survival of patients. For example, cirrhosis is the seventh leading cause of death and the fourth disease related cause of death in people between the ages of 25 to 44. (Source: American Liver Foundation).

In acute liver disease, the liver is able to regenerate after being injured. If the disease progresses beyond the liver's capacity to regenerate new cells, the body's entire metabolism is severely affected. Loss of liver function may result in metabolic instability combined with disruption of essential bodily functions (i.e., energy supply, acid-base balance and thermoregulation.) If not rapidly reversed, complications such as uncontrolled bleeding and sepsis occur, and dependent organs such as the brain and kidneys cease to function because of toxic by-products or because the liver is no longer synthesizing important nutrients. After large liver damage, liver tissue looses its regenerative and metabolic functions, and liver transplantation is a therapeutic strategy commonly used. However, the clinical application of liver transplantation is limited by the availability of human hepatocytes, liver tissue and the number of liver cells that can be transplanted safely at one time. Moreover, latence before surgery and post-surgery complications could be critical to counteract the acute phase of liver failure. Another therapeutic strategy consists in a liver resection (removal of a portion of the liver). The most typical indications for liver resection are a malignant tumor, a hepatocellular carcinoma or a proliferative biliary diseases including cholangiocarcinoma. Tumors can be primary (developed in the liver) or metastatic (developed in another organ, then migrated to the liver). The majority of liver metastases come from the colon. The single tumor or more than one tumor confined to either left or right side of the liver can be successfully resected with 5-year survival as high as 60%. Liver resections performed on patients with extrahepatic disease may relieve the symptoms caused by the tumor, but offer little improvement in survival. Benign tumors of the liver (adenoma, and focal nodular hyperplasia) can be successfully managed by liver resection as well. Liver resections are also performed on people willing to donate part of their liver.

Taking into account the importance of liver transplantation and liver resection, Several strategies have been suggested to stimulate liver regeneration and suppress or limiting liver failure in the case of liver resection or transplantation.

Liver cell is believed to be controlled by various growth stimulatory and growth inhibitory cytokines of autocrine or paracrine origin, however, the exact role and action mechanism of these growth factors is far from entirely understood. Cytokines are secreted peptides or proteins that regulate the intermediary metabolism of amino acid, proteins, carbohydrates, lipids and minerals. Cytokines include peptides or proteins that act to mediate inflammation and are involved in intracellular communication modulating cell proliferation, and adhesion of inflammatory cells to the walls of the vessels, and to the extra cellular matrix. Cytokines are essential for the communication between the liver and extrahepatic sites and within the liver itself. Cytokines interact with hormones such as glucocorticoids, resulting in a complex network of mutual control. Many cytokines exert growth activity in addition to their specific proinflammatory effects. The liver is an important site of cytokine synthesis and the major clearance organ for several cytokines. In liver disease, cytokines are involved in the onset of intrahepatic immune responses, in liver regeneration, and in the fibrotic and cirrhotic transformation of the liver.

Liver cell is also believed to be controlled by various growth factors. Growth factors are required to regulate developmental events or required to regulate expression of genes encoding other secreted proteins that may participate in intracellular communication and coordination of development and includes, insulin-like growth factor-I and II (IGF I and II), epidermal growth factor (EGF), type a and type b transforming growth factor (TGF-α and TGF-β), platelet-derived growth factor (PDGF).

In vitro, DNA synthesis in isolated hepatocytes has been shown to be stimulated by growth factors such as TGFα, or EGF. A further protein, named hepatocyte growth factor (HGF) has been shown to be a mitogen for primary hepatocytes.

Based on these observations, it has been proposed that these factors may be important mediator of liver regeneration. Consequently, growth factors as TGFα, EGF or HGF with growth factor-like activities have been indicated in the treatment of liver regeneration. However, these therapeutic strategies, suggested to stimulate liver regeneration and suppress liver failure, have not proved their efficacity without toxicity, and adverse effects. Namely, these growth factor favor tumor progression (Gang-Hong, et al., 1992; Lee 1992; Horiguchi, et al. 2002).

Consequently, there remains a need in the art for an effective method which would stimulate liver regeneration, would protect against liver failure, and would be deprived of adverse toxic and tumorigenic effects. This need exists in any patient population in which liver damage has been induced. This need exists not only for transplanted patients but also for donors, and patients having undergone a liver resection. Further, there is still a need in the art for novel therapeutically useful compounds, which stimulate liver regeneration.

Additionally, taking into account the poor availability of donor organs, living donor partial liver transplantation is recognized as a measure for overcoming the lack of organs, and facilities for partial liver transplantation. However, partial liver transplantation cannot be considered as a safe operation for adults representing the majority of transplantation patients because the resectable liver weight of donors is often less than the necessary liver weight for recipients. Thus there is a need for a mean for safe and rapid liver regeneration for small grafts.

Accordingly, it is an object of the present invention to provide a mean for the stimulation of liver regeneration after partial resection. An object of the present invention is also to provide a drug that can promote liver regeneration or hepatocyte growth after liver transplantation such as partial liver transplantation, and also after the occurrence of a discare causing liver failure, such as cirrhosis, acute hepatitis and chronic hepatitis.

These and further objects will be apparent to one ordinary skill in the art.

SUMMARY OF THE INVENTION

The present invention is based on the experimental finding that HIP/PAP has mitogenic and antiapoptotic effects in vitro on hepatocytes in primary culture. Moreover, HIP/PAP is a mitogenic and anti-apoptotic molecule for hepatocytes, in vivo, during liver failure and liver regeneration. The present invention is also based on the experimental finding that HIP/PAP has no adverse effects in mammals.

A first object of the invention consists in a pharmaceutical composition for stimulating liver regeneration in vivo comprising an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1, in combination with at least one physiologically acceptable excipient.

In another aspect, the present invention relates to a pharmaceutical composition for stimulating liver regeneration in vivo comprising an effective amount of the human hepatocarcinoma-intestine-pancreas/pancreatic-associated protein (HIP/PAP) of sequence SEQ ID No 1, in combination with at least one physiologically acceptable excipient.

The present invention also relates to a pharmaceutical composition with limited adverse effects on liver necrosis comprising:
(i) a therapeutically effective amount of a hepatotoxic compound,
(ii) a liver damage effective amount of a polypeptide as defined above.

The enhancer (2 kb) and promoter (0.3 kb) of the regulatory regions of the mouse albumin gene are indicated by dotted lines. Exons II, III, IV, V and VI and introns of the human HIP/PAP gene (1.6 kb) are indicated by black boxes and a dotted line, respectively. The bovine growth hormone poly A fragment (1021-1235) pcDNA 3.1 is indicated by a dotted line. Plasmid DNA is indicated by the heavy line. Relevant restriction sites are indicated by the arrows.

Figure 2:
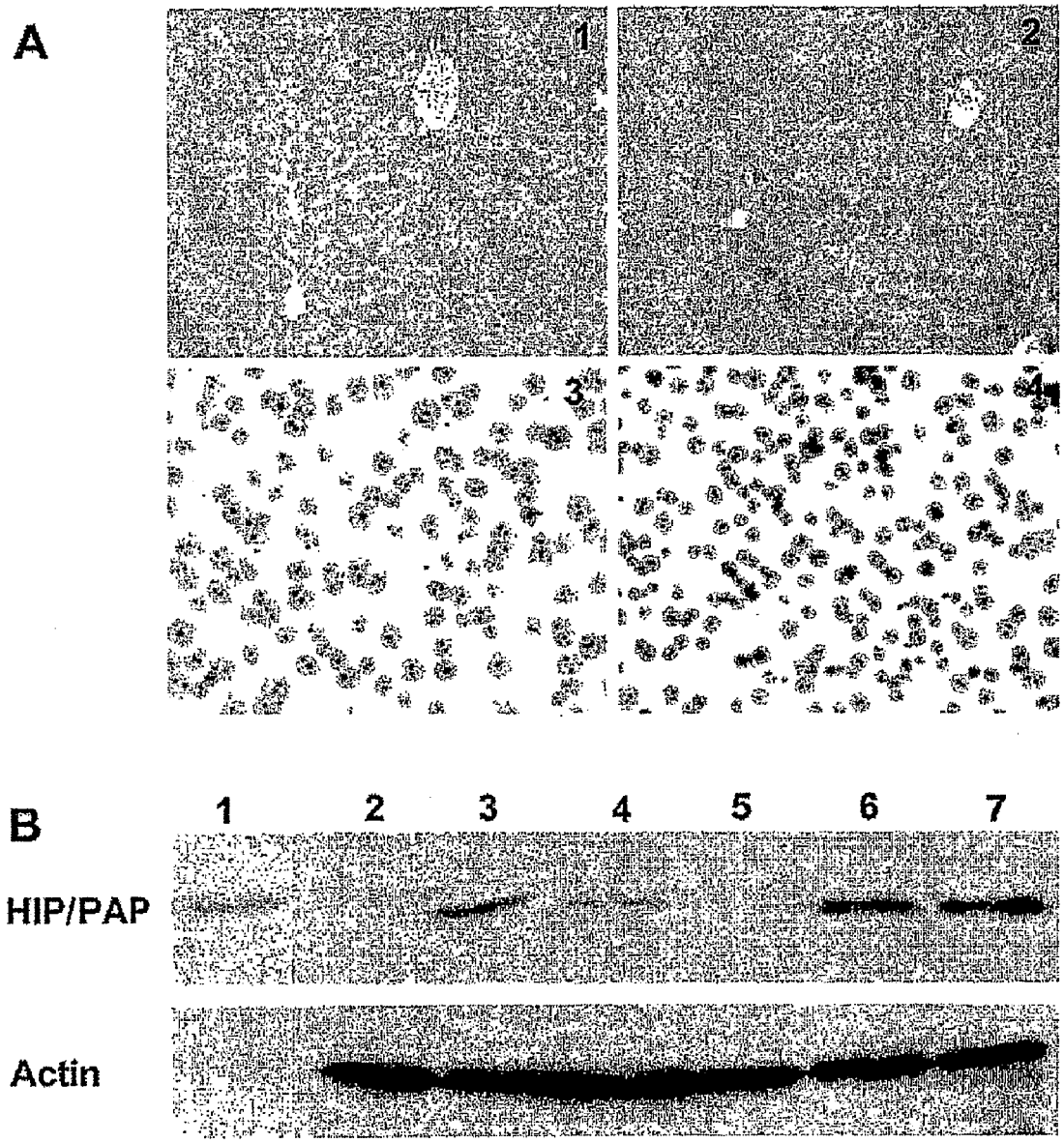

FIG. 2 Immunodetection of HIP/PAP protein.
A. Immunohistochemistry: original magnification ×20, 1 wild-type liver, 2 HIP/PAP transgenic liver, 3 wild-type hepatocytes, 4 HIP/PAP hepatocytes.
B. Western blot hybridised with HIP/PAP and actin antibodies showing a band with the 16 kDA and the 45 kDa expected size, respectively. Lane 1 purified HIP/PAP protein (10 ng), lanes 2, 3 and 4, wild-type liver; HIP/PAP transgenic liver 27 and 24 homozygous strains, respectively, lanes 5, 6 and 7 wild-type, HIP/PAP 27 and 24 hepatocytes after isolation, respectively.

Figure 3:
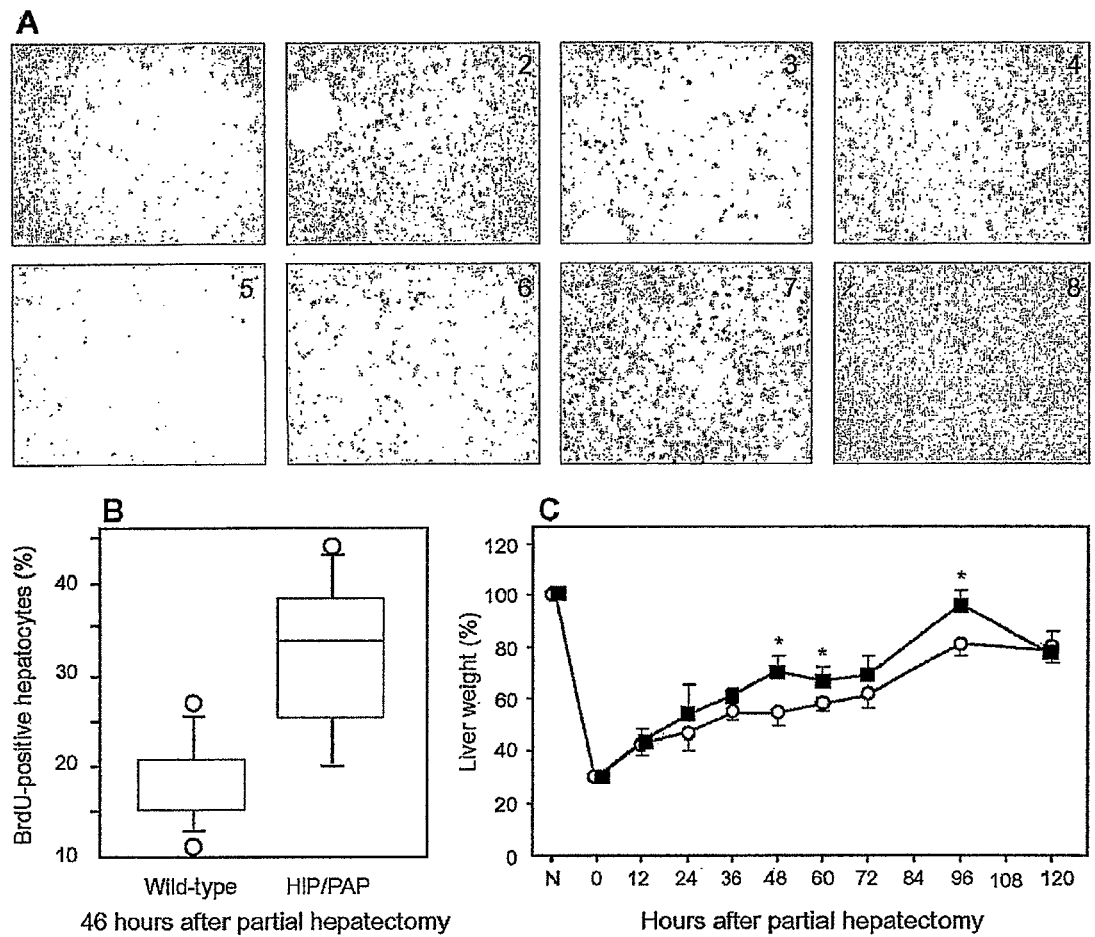

FIG. 3 Time course of in vivo hepatic regeneration after partial hepatectomy.
A. Immunodetection of BrU-positive nuclei, in wild-type (1, 2, 3, 4) and HIP/PAP transgenic livers (5, 6, 7, 8); 1 and 5 24 hours, 2 and 6 36 hours, 3 and 7 46 hours, 4 and 8 55 hours after hepatectomy.
B. Each box plot comprises five horizontal lines displaying the $10^{th}$, $25^{th}$, $50^{th}$, $75^{th}$, percentiles of a variable. All values for the variable above the $90^{th}$ percentile and below the $10^{th}$ percentile are plotted separately, so that the box plots are valuable in highlighting any outliers. Wild-type mice (n=9), and HIP/PAP transgenic mice (n=10) (p=0.0014).
C. Liver weights were measured in normal non hepatectomized mice. The liver/body ratio of weight was calculated and expressed as the average percentage ±SD. There was no difference in this ratio between the two groups (0.0460±0.0064, n=12 and 0.0489±0.0035 n=16 for wild-type and HIP/PAP transgenic mice, respectively). The average percentage recovery of normal liver weight (±sd) in wild type (○) and HIP/PAP mice (■) at various time points after partial hepatectomy shows stimulated recovery in the HIP/PAP transgenic mice (5 to 9 mice were hepatectomized at each time for each group) The difference was statistically significant at 48 hours (p<0.001), 60 hours (p<0.003) and 96 hours (p<0.002).

Figure 4:
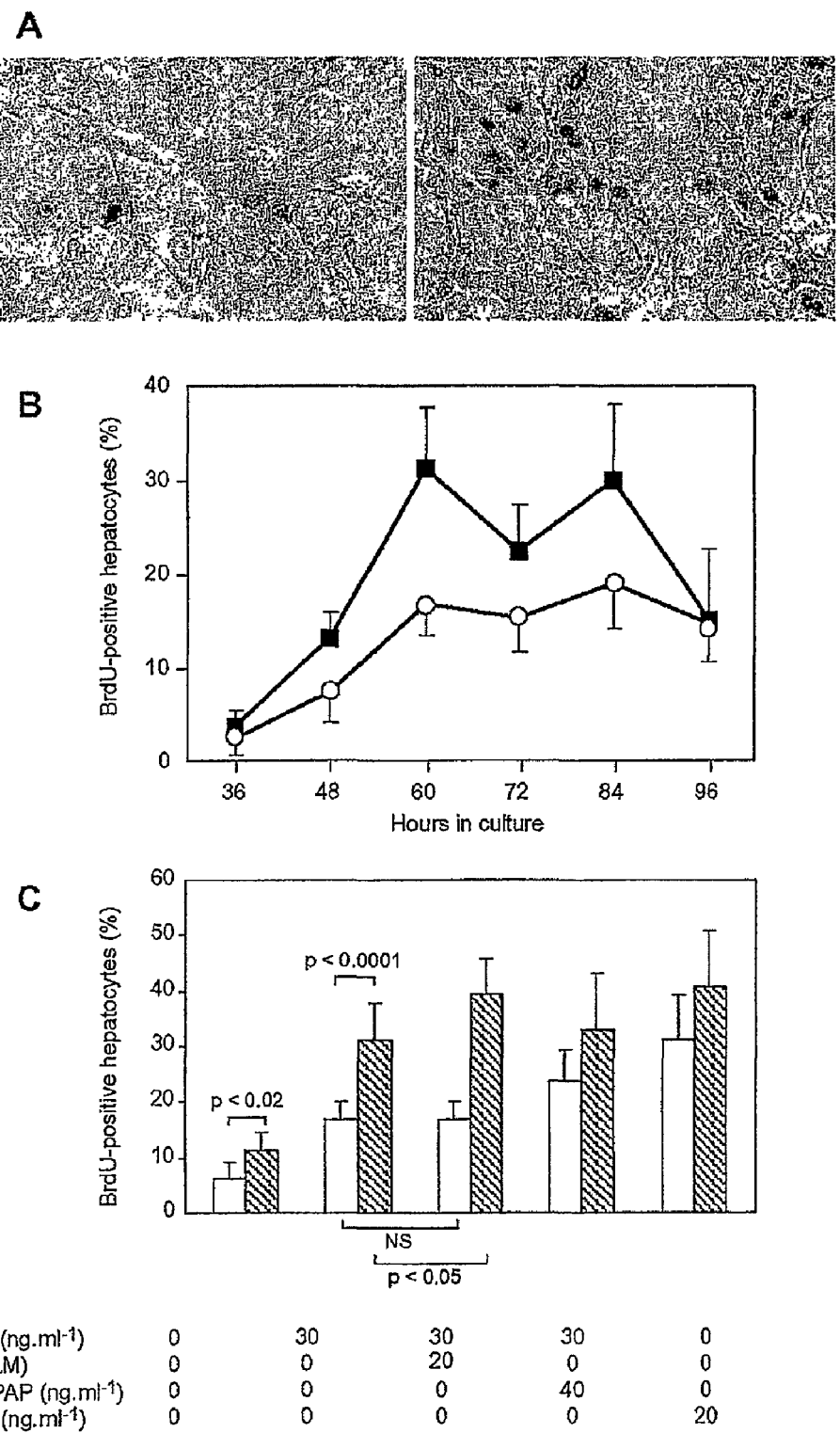

FIG. 4 DNA Synthesis in wild-type and HIP/PAP transgenic hepatocytes.
A. Immunodetection of BrU-positive hepatocytes at 60 hours, wild-type (a), HIP/PAP (b) (original magnification ×200). The values shown are the mean±SD of independent cultures from 12 mice of each genotype.
B. time-course of DNA synthesis in hepatocytes stimulated by EGF (30 ng·ml$^{-1}$), wild-type (○), HIP/PAP (■).
C. DNA synthesis in cultured hepatocytes 60 hours after plating: Growth Factors (EGF 30 ng ml$^{-1}$, HIP/PAP 40 ng ml$^{-1}$) were added after cell attachment. Forskolin was added for the last 16 hours. The data from 4 to 20 of experiments were presented as mean±SD (□) wild-type, (■) HIP/PAP.

Figure 5:
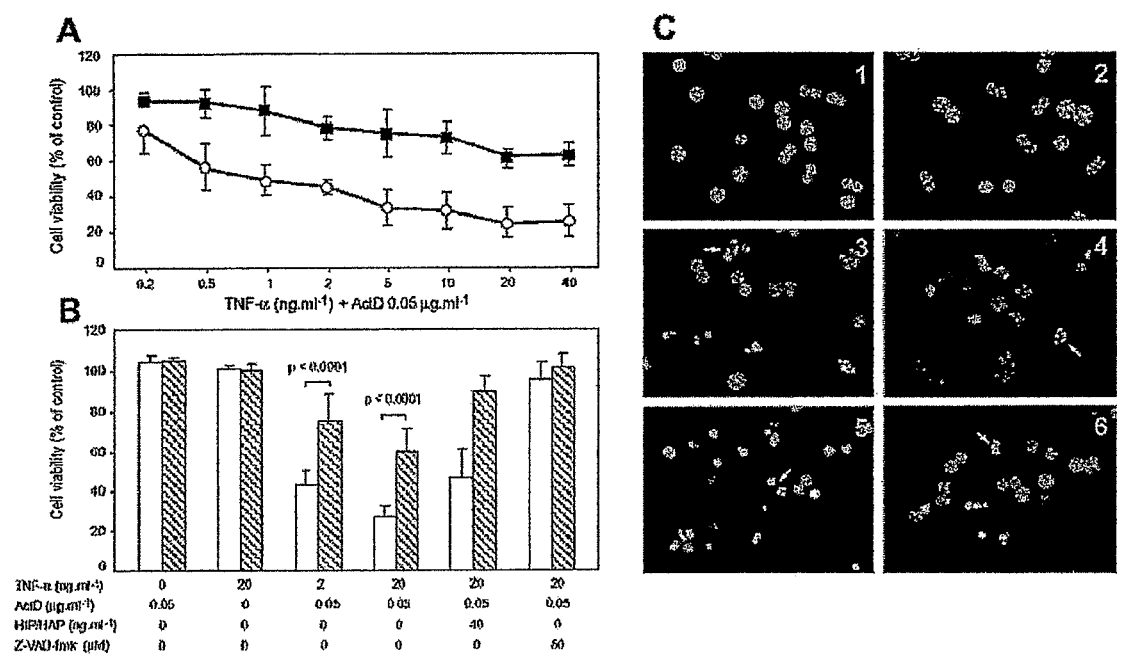

FIG. 5 HIP/PAP inhibits TNF-α+ActD-induced apoptosis in cultured primary hepatocytes.
A. Dose-dependent TNF-α reduction in cell viability in wild-type (□) and HIP/PAP (■) transgenic hepatocytes. The data presented are the mean±s.e.m of independent cultures with four replicates from five mice of each genotype.
B. Hepatocytes were treated as indicated for 17 hours, wild-type (□), HIP/PAP (■). The histograms represent the mean values±s.e.m. of three separate experiments with four replicates.
C. Pyknotic nuclei of hepatocytes still attached were stained with Hoechst 33258 (magnification ×400). Arrows indicate features of apoptotic bodies organized in "rosettes" characteristic of the hepatocyte apoptosis induced by TNF-α, wild-type (1, 3, 5) HIP/PAP (2, 4, 6) control cultures: no addition (1 and 2), TNF-α 2 ng ml$^{-1}$+ActD (3 and 4), TNF-α 20 ng ml$^{-1}$+ActD (5 and 6).

Figure 6:
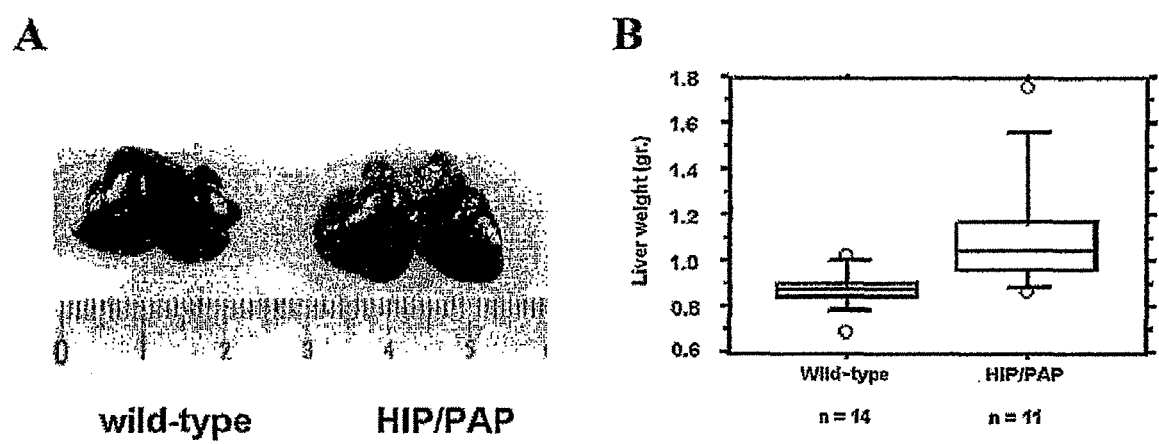

FIG. 6 Stimulation of liver regeneration in SCID mice transplanted with hepatocytes from wild-type or HIP/PAP transgenic mice.
A. Macroscopic evaluation of the livers of SCID mice, transplanted with hepatocytes from wild-type or HIP/PAP transgenic mice, and killed 7 days after hepatectomy.
B. Box plots of the liver weights of hepatocyte-transplanted SCID mice 7 days after hepatectomy. A significant difference was observed (p=0.0008) between SCID transplanted with wild-type hepatocytes versus SCID transplanted with HIP/PAP hepatocytes, by using the Mann-Whitney test.

Figure 7:
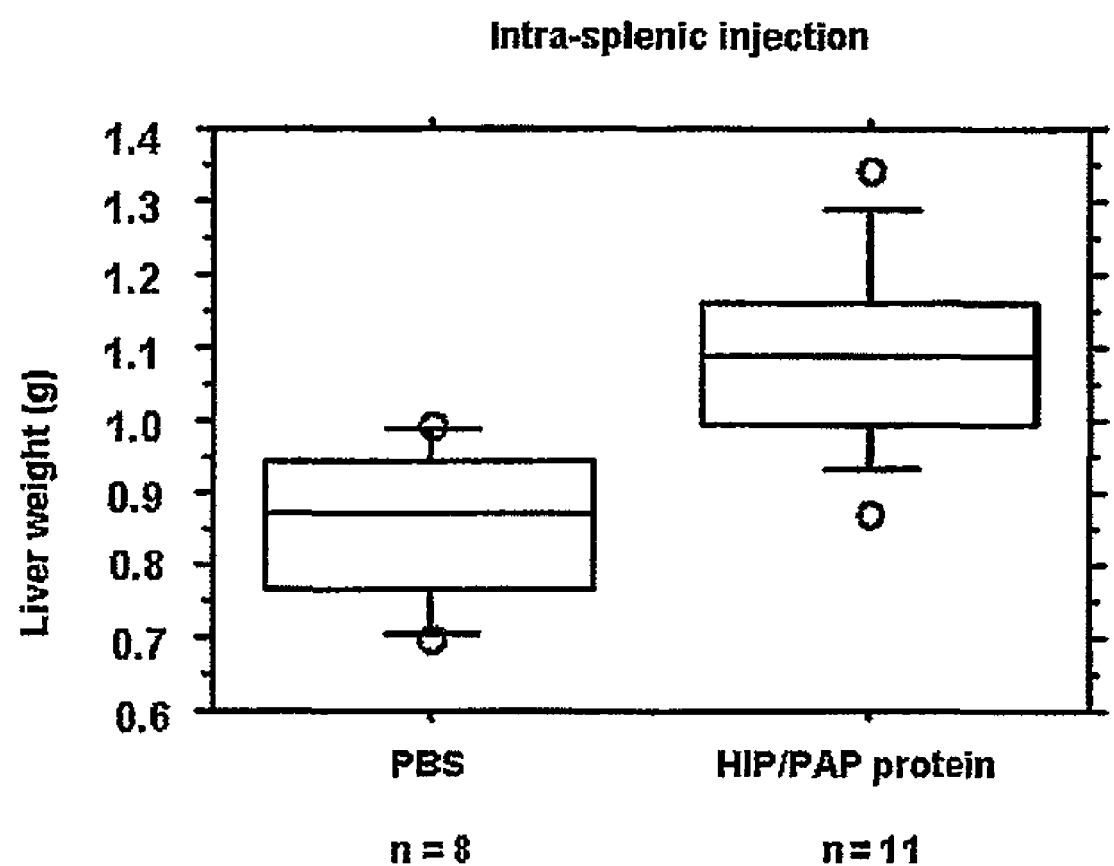

FIG. 7 Stimulation of liver regeneration in SCID mice by HIP/PAP protein.

Box plots of the liver weights of SCID mice intra-splenic injected 36 hours after partial hepatectomy with HIP/PAP protein (600 ng/mice) or phosphate buffer saline (PBS) (100 µL). Mice were killed 7 days after hepatectomy. A significant difference was observed (p=0.0022) between SCID injected with HIP/PAP protein versus SCID injected with PBS, by using the Mann-Whitney test.

Figure 8:
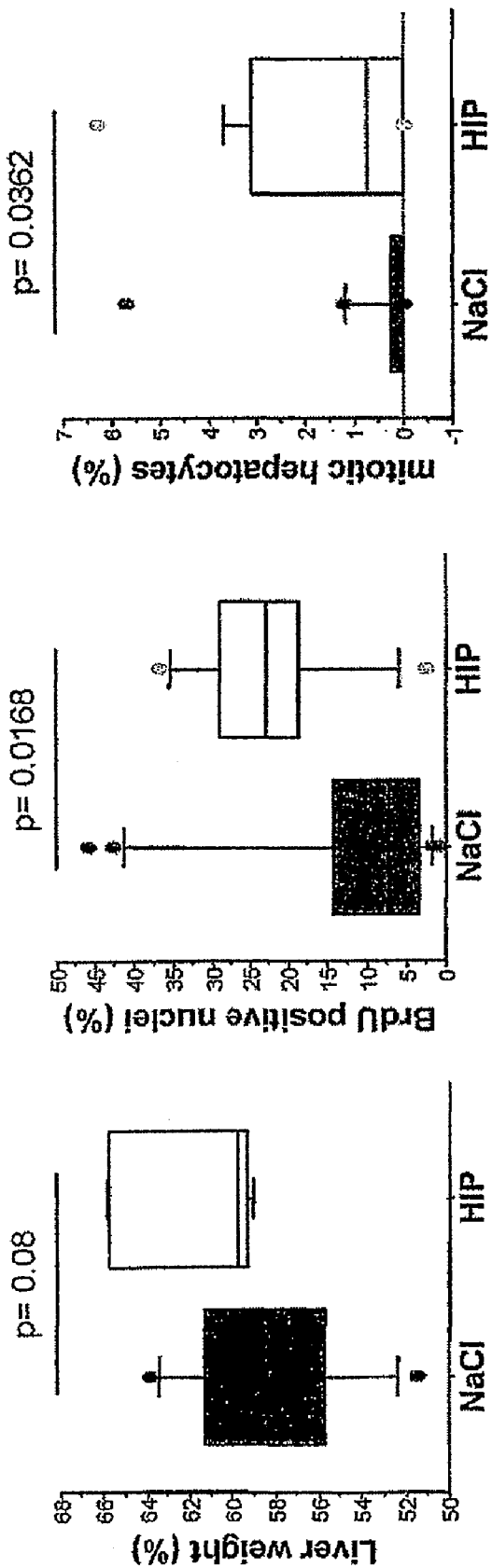

FIG. 8 HIP/PAP protein injection stimulates liver regeneration in C57 mice.

The effect of the HIP/PAP protein versus saline injected immediately after partial hepatectomy of C57Bl6, on the restoration of the hepatic mass, the incorporation of BrdU and mitosis, 46 hours after partial hepatectomy, has been compared. Box plots representing the hepatic mass, the incorporation of BrdU and mitosis are presented. A Mann-Whitney test has been realised, and $p<0.05$ is considered statistically significant.

Figure 9:
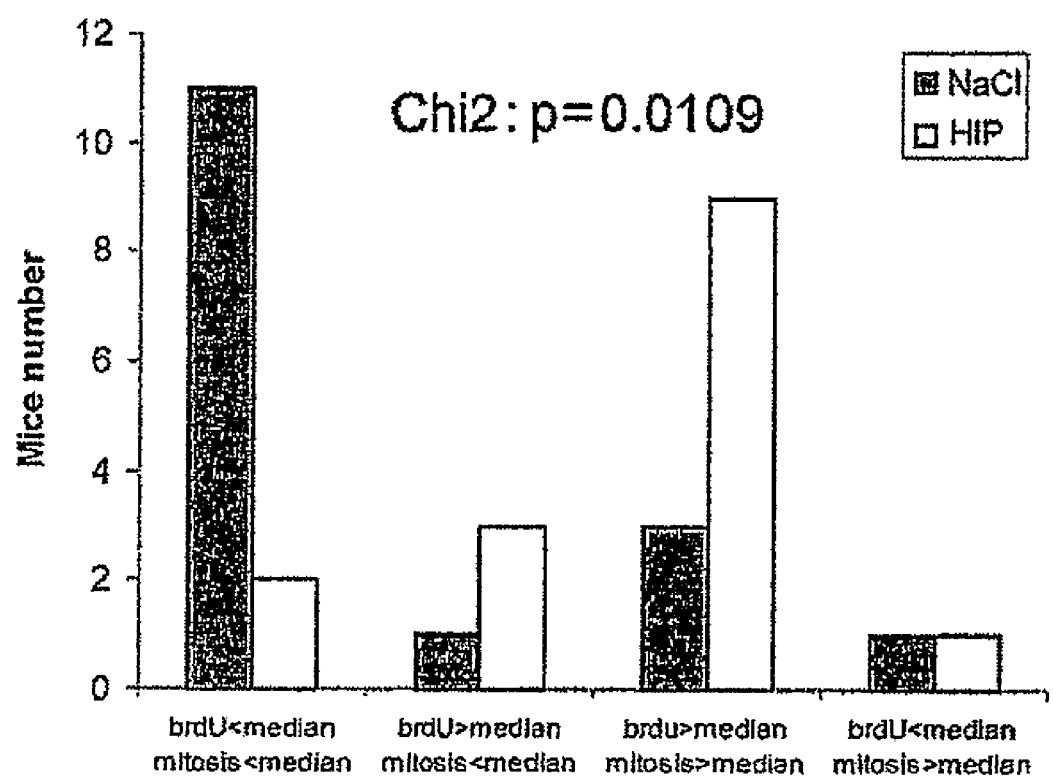

FIG. 9 Statistical analysis of mice population according to BrdU and mitosis.

The distribution is statistically different between groups, which are defined according to combined median for the BrdU incorporation and mitosis 46 hours after partial hepatectomy.

Figure 10:
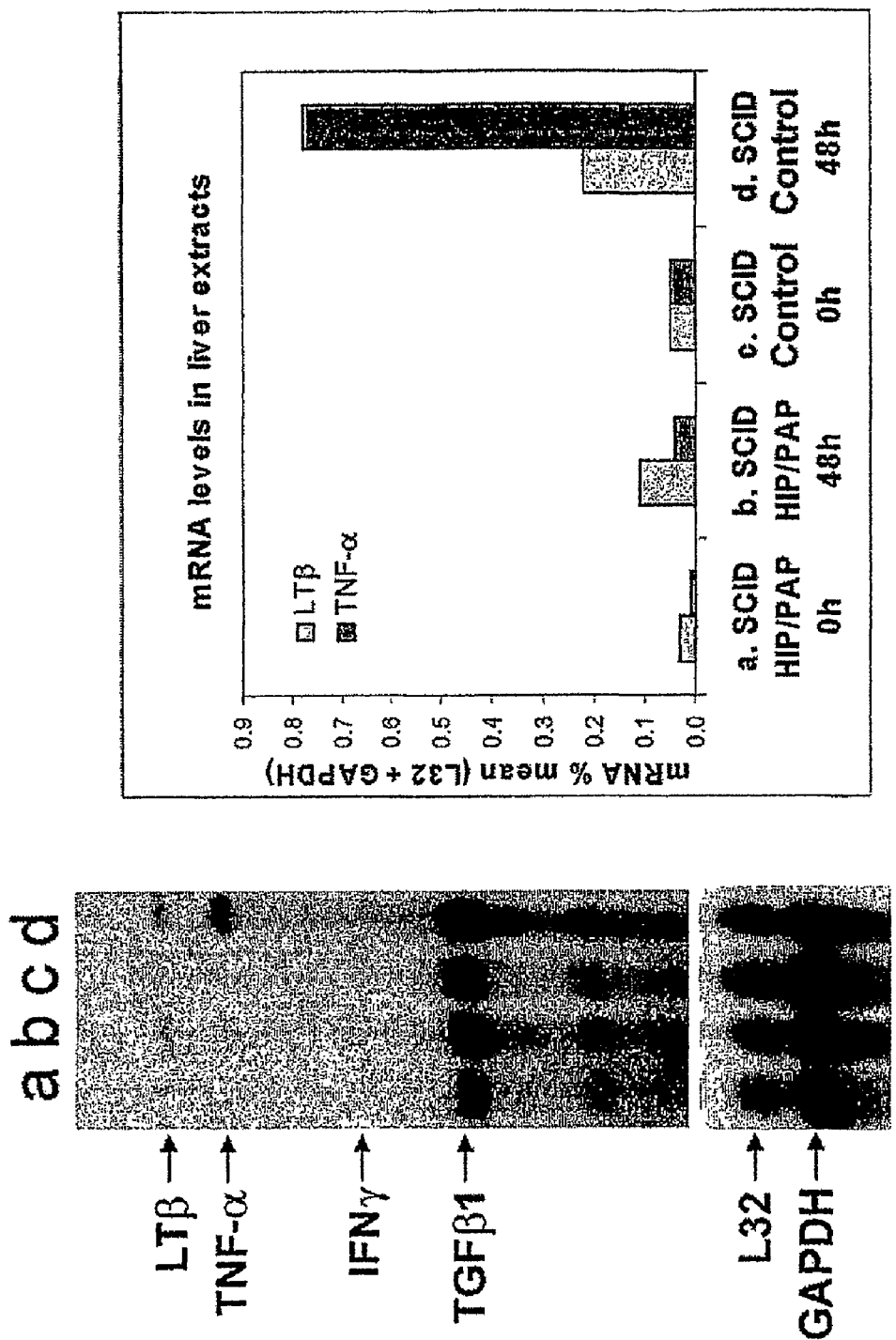

FIG. 10 Hepatic cytokines expression in the liver of transplanted mice after hepatectomy cytokine expression in the liver at T0 of PHX (partial hepatectomy) and after 46 hours of SCID mice transplanted with HIP/PAP versus control hepatocytes has been compared. Rnase protection methodology allowed to compare in the same experiment lymphotoxin-β (LTβ), TNF-α, and TGF-β in a pool of 4 liver extracts HIP/PAP transgenic mice lanes a and b; SCID mice lanes c and d at T0 (lanes a and c) and at T46 hours post PHX (lanes b and d). Densitometric analysis quantified the signals which have been normalized versus two house keeping genes (L32 and GAPDH). mRNA levels have also been measured in liver extracts. The graph represents for each group of mice, the mean of L32 and GAPDH mRNA content.

Figure 11:
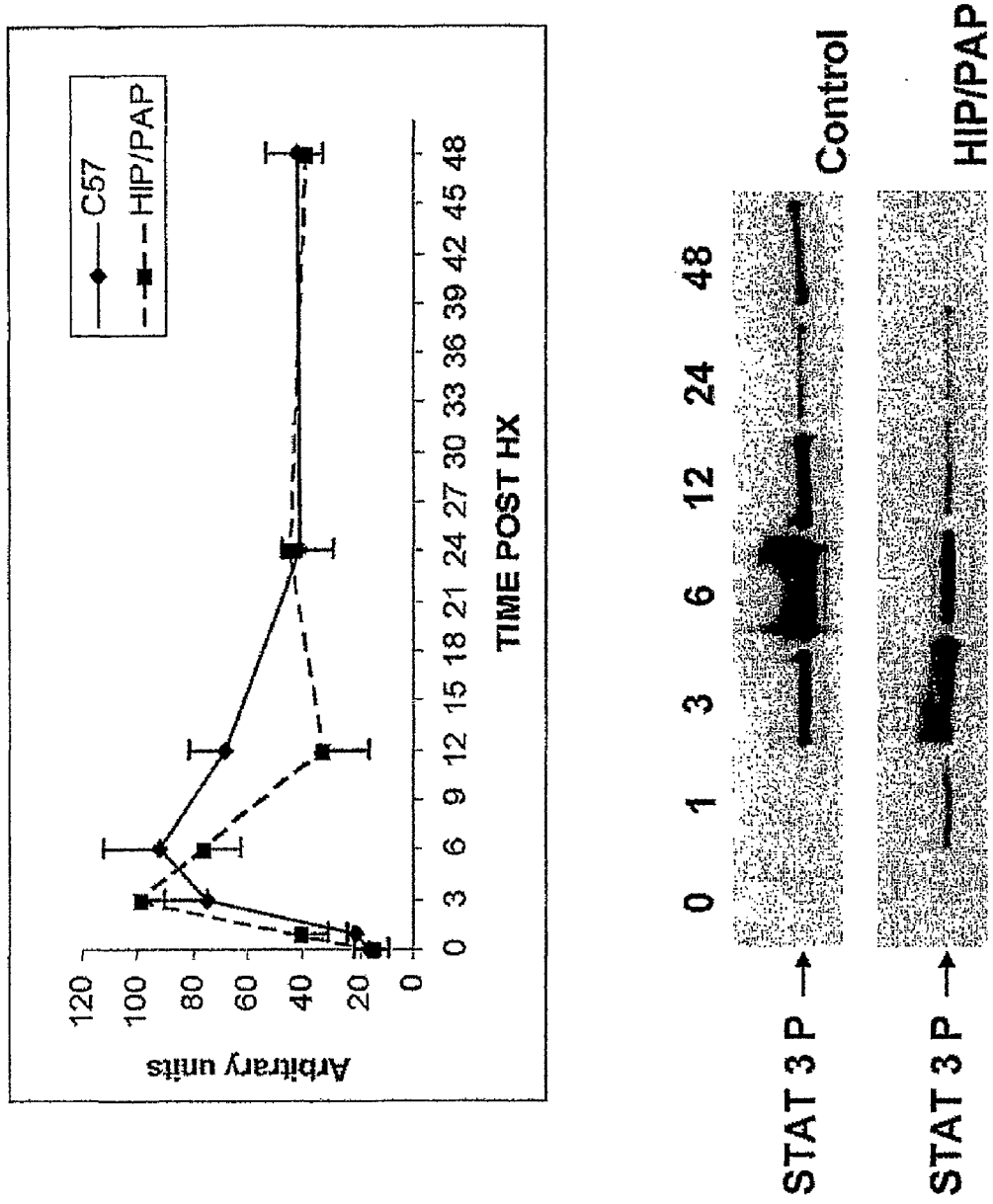

FIG. 11 Stat 3 activation post-hepatectomy accumulation/degradation time course of nuclear phospho-STAT3 was measured in HIP/PAP transgenic versus C57Bl6 mice, during the first 24 hours after partial hepatectomy (FIG. 11). Activation was detected as soon as 1 hour post PHX in HIP/PAP but not in C57Bl6 mice (p=0.02). Moreover, STAT3 activation was back to lower levels in HIP/PAP than in C57Bl6 mice (p=0.04), as soon as 12 hours. The results were validated and visualized by western blot analysis with anti-STAT3 phosphorylated antibodies.

Figure 12:
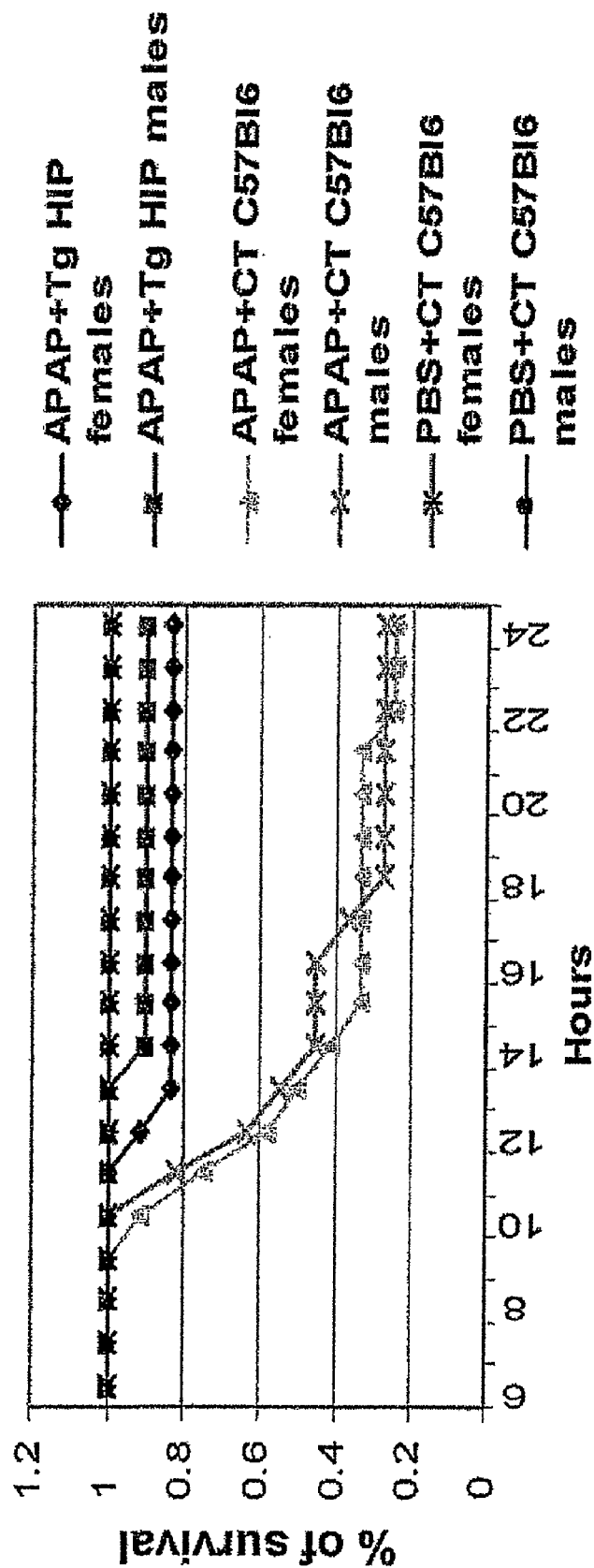

FIG. 12 HIP/PAP transgenic mice are protected against acute liver failure induced by acetaminophen (APAP)

The survival of Female HIP/PAP transgenic mice (Tg HIP females) and male HIP/PAP transgenic mice (Tg HIP males) treated by a lethal dose of APAP (acetaminophen) (1000 mg·kg$^{-1}$), has been compared to the survival of C57Bl6 control mice (CT C57Bl6 males and females), treated by APAP or PBS. A significant difference in survival was observed between HIP/PAP transgenic mice injected with APAP versus C57Bl6-control mice injected with APAP. HIP/PAP has also a preventive effect against APAP intoxication.

Figure 13:
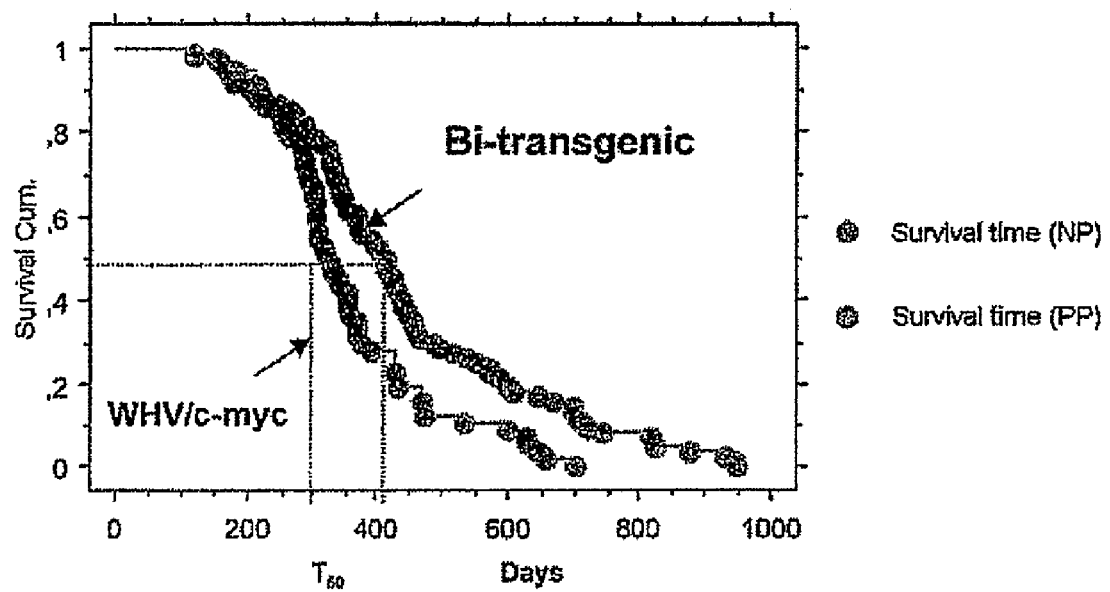

FIG. 13 HIP/PAP exhibits no toxic effects during long-term in vivo follow-up

HIP/PAP transgenic mice (metallothionéine promoter) were crossed with WHV/c-myc mice in which the liver-specific expression of c-myc driven by woodchuck hepatitis (WHV) regulatory sequences causes liver cancer in all animals. Survival curves showed that the T50 of bitransgenic mice was 60 weeks (n=87 mice) versus 42 weeks for the T50 of WHV/c-myc oncomice (n=39 mice), Survival curves were identical for HIP/PAP transgenic mice and for littermate negative controls. Thus, firstly, toxicity of HIP/PAP protein during the lifespan of these mice has not been detected and HCC onset is delayed in mice carrying both transgenes, i.e. WHV/c-myc and HIP/PAP.

DETAILED DESCRIPTION OF THE INVENTION

The inventors have found according to the invention that HIP/PAP has mitogenic and antiapoptotic effects in vitro on hepatocytes in primary culture. Moreover, HIP/PAP is a mitogenic and anti-apoptotic molecule for hepatocytes, in vivo, during liver failure and liver regeneration.

The human hepatocarcinoma-intestine-pancreas/pancreatic-associated protein (HIP/PAP) gene was identified because of its increased expression in 25% of human hepatocellular carcinoma by using Northern blot analysis (Lasserre et al., 1992). It had been shown that HIP/PAP protein is detected in normal subjects in the intestine (Paneth and neuro-endoctine cells) and the pancreas (acinar pancreatic cells and islets of Langerhans). The HIP/PAP protein is also detected in some potential progenitor liver cells around portal area of normal liver (Christa et al., 1999). HIP/PAP is rapidly overexpressed during the acute phase of pancreatitis. It also acts as an adhesion molecule for rat hepatocytes and interacts with extracellular matrix proteins such as laminin-1 and fibronectin. This protein contains a putative signal peptide, and thus belongs to group VII of the C-type lectin family, according to Drickamer's classification and structural analysis (Abergel et al., 1999).

Now, the inventors have found that liver regeneration is stimulated, in vivo, in mice expressing the human HIP/PAP gene, after partial hepatectomy. Additionally, It has been found according to the invention that HIP/PAP has a mitogenic effect also in vitro in primary culture hepatocytes. In another aspect, it has also been found according to the invention that HIP/PAP has an anti-apoptotic effect against apoptosis induced by TNF-α combined with actinomycin D in primary culture hepatocytes. It has also been shown according to the invention that hepatocytes that recombinantly express HIP/PAP induce liver regeneration, when injected locally in partially liver-resected mice. The inventors have shown that the HIP/PAP protein, when injected to mice having undergone partial hepatectomy, induces liver regeneration. Taking these observations into account, the inventors have shown that the HIP/PAP protein provides effective mitogenic and anti-apoptotic effects, and protects against liver failure, in vivo, has no adverse effects and is particularly devoid of any carcinogenic effect, in contrast to the growth factors known in the art such as HGF, TGFα or EGF, as described above.

Taken together, these results demonstrate the therapeutic importance of HIP/PAP in liver regeneration. Thus, these experimental results have allowed the inventors to design pharmaceutical compositions for stimulating liver regeneration in vivo comprising an effective amount of the human hepatocarcinoma-intestine-pancreas/pancreatic-associated protein (HIP/PAP) of sequence SEQ ID No 1, in combination with at least one physiologically acceptable excipient.

A first object of the invention consists in a pharmaceutical composition for stimulating liver regeneration in vivo including after chronic/acute liver failure, comprising an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1, in combination with at least one physiologically acceptable excipient.

The invention also concerns a pharmaceutical composition comprising a polypeptide fragment of HIP/PAP, which is effective for liver regeneration. This polypeptide of sequence starting at the amino acid residue 36 and ending at the amino acid residue 175 of sequence SEQ ID No 1 consists of a biologically active portion of the HIP/PAP protein, which had previously been described as a Carbohydrate Recognition Domain (CRD) sequence (Christa et al. 1994).

In a first preferred embodiment, the pharmaceutical composition of the invention comprises a biologically active portion of HIP/PAP as described hereabove, which can be isolated from cell or tissue sources by an appropriate purification scheme using standard protein purification techniques.

In another preferred embodiment of said pharmaceutical composition the biologically active portion of HIP/PAP is produced by recombinant DNA techniques, such as described in the examples. According to a third preferred embodiment, the biologically active portion of HIP/PAP is synthetised chemically using standard peptide synthesis techniques.

An isolated or purified biologically active portion of HIP/PAP is substantially free of cellular material or other contamination proteins from the cell or tissue source from which HIP/PAP is derived, or substantially free from chemical precursors when chemically synthetised.

To determine the percent of identity of two amino acid sequences, the sequence are aligned for optimal comparison purposes. For example, gaps can be introduced in one or both of a first and a second amino acid sequence for optimal alignment and non-homologous sequences can be disregarded for comparison purposes.

For optimal comparison purposes, the percent of identity of two amino acid sequences can be achieved with CLUSTAL W (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)=<<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none>>; (12) MATRIX=<<default>>; (13) GAP OPEN=<<default>>; (14) END GAPS=<<default>>; (15) GAP EXTENSION=<<default>>; (16) GAP DISTANCES=<<default>>; (17) TREE TYPE=<<cladogram>> et (18) TREE GRAP DISTANCES=<<hide>>.

Biologically active portions of HIP/PAP include peptides comprising amino acid sequences sufficiently homologous to the full length amino acid sequence of HIP/PAP of SEQ ID No 1, which include the same number of amino acids than the full length HIP/PAP, and exhibit at least the same biological activity than HIP/PAP.

Biologically active portions of HIP/PAP include further peptides comprising amino acid sequences sufficiently homologous to the full length amino acid sequence of HIP/PAP of SEQ ID No 1, which include more amino acids than the full length HIP/PAP, and exhibit at least the same biological activity than HIP/PAP.

By the "same biological activity", as applied to biologically active peptides homologous to HIP/PAP, it is herein intended peptides that induce in vivo liver regeneration with the same order of magnitude than the full length HIP/PAP, as it can be easily determined by the one skilled in the art, for example by measuring BrdU incorporation by heparocytes, and measuring liver mass restoration as it is shown in Example 2.

As used herein the biologically active portion of HIP/PAP encompasses a polypeptide comprising an amino acid sequence having 90% of identity with the polypeptide of sequence starting at the amino acid residue 36 and ending at the amino acid residue 175 of sequence SEQ ID No 1. According to the invention a first amino acid sequence having at least 90% of identity with a second amino acid sequence, comprises at least 90%, and preferably at least 91%, 92%, 93%, 94%, 95%, 96%, 97%, 98%, or 99% of identity in amino acids with said second amino acid sequence.

Polypeptides according to the invention comprise also variants, such as the CRD sequence from different mammals, and for example from the bovine pancreatic thread protein (BPTP) or the pancreatic associated protein 1 (PAP1) from the rat, described by Orelle, et al.

In addition to naturally occurring allelic variants of the biologically active portion of HIP/PAP sequences that exist in mammals, the person skilled in the art will further appreciate that changes can be introduced by mutation into the nucleotide sequence of SEQ ID No 1, thereby leading to changes in the amino acid sequence of HIP/PAP without altering the biological activity of HIP/PAP.

In addition, substitutions of non-essential amino acid can be made in the sequences corresponding to HIP/PAP. A "non essential" amino acid residue is an amino acid residue that can be altered from the wild type sequence of HIP/PAP without altering the biological activity, whereas an "essential" amino acid residue is required for biological activity.

A second object of the invention consists in a pharmaceutical composition for stimulating liver regeneration in vivo comprising a polypeptide of sequence starting at the amino acid residue 36 and ending at the amino acid residue 175 of sequence SEQ ID No 1, in combination with at least one physiologically acceptable excipient.

Another object of the invention is a pharmaceutical composition for stimulating liver regeneration in vivo comprising an effective amount of a polypeptide comprising an amino acid sequence having 90% amino acid identity with the polypeptide consisting of the amino acid sequence starting at the amino acid residue 27 and ending at the amino acid residue 175 of sequence SEQ ID No 1, in combination with at least one physiologically acceptable excipient.

A further object of the invention consists in a pharmaceutical composition according to claim 1 comprising an effective amount of the polypeptide consisting of the amino acid sequence starting at the amino acid residue 27 and ending at the amino acid residue 175 of sequence SEQ ID No 1, in combination with at least one physiologically acceptable excipient.

Another object of the invention consists in a pharmaceutical composition for stimulating liver regeneration in vivo comprising an effective amount of the human hepatocarcinoma-intestine-pancreas/pancreatic-associated protein (HIP/PAP), in combination with at least one physiologically acceptable excipient.

Without wishing to be bound to any particular theory, the inventors believe that the complete HIP/PAP protein of sequence SEQ ID No 1, i.e. a polypeptide comprising the CRD sequence, a signal peptide, and a pro-peptide, leads to a best folding of said protein, particularly when said protein is produced through DNA recombinant techniques in eukaryotic cells that have been transfected with an expression cassette encoding it. By the way, a correct folding of the therapeutically active HIP/PAP may lead to a best biological efficiency for the pharmaceutical composition comprising said protein, for liver regeneration compared to a composition comprising only a portion of the protein.

In a preferred embodiment, HIP/PAP has the amino acid sequence shown in SEQ ID No 1. In other embodiments, HIP/PAP is substantially identical to SEQ ID No 1 and retains the same biological activity, for liver regeneration, when compared to the protein of sequence SEQ ID No 1, but differs in amino acid sequence due to natural allelic variations or mutagenesis. Accordingly, in another embodiment HIP/PAP is a protein which comprises an amino acid sequence of at least about, 90%, and preferably 91%, 92%, 93%, 94%, 95%, 96%, 97%, 98%, 99%, or more identity with the amino acid sequence of SEQ ID No 1.

The invention also encompasses HIP/PAP chimeric or fusion proteins. As used herein, a chimeric protein or a fusion protein comprises the polypeptides cited above which are fused to a non-HIP/PAP polypeptide. Within the fusion protein, the HIP/PAP polypeptide and the non-HIP/PAP polypeptide are fused to each other. The non-HIP/PAP polypeptide can be fused to the N-terminus or to the C-terminus of the HIP/PAP polypeptide.

For example, in one embodiment, the fusion protein is a GST-HIP/PAP fusion protein in which the HIP/PAP sequence is fused to the C-terminus of the GST sequence. Such fusion proteins can facilitate the purification of recombinant HIP/PAP.

In all cases the fusion proteins of the invention possess the same biological activity as HIP/PAP of SEQ ID No 1.

Two different pathways trigger liver regeneration, one causes the replication of differentiated hepatocytes or biliary cells after partial hepatectomy or bile duct ligation (Fausto et al., 1994, Fausto et al., 2000). The second regenerative pathway is triggered after toxic injury, on massive necrosis or carcinogenesis, when the proliferation of hepatocytes or biliary cells is impaired or slowed by the injury (Factor V M et al., Petersen B et al., (1998), Akhurst B et al.). Under these conditions, it has been proposed <<stem-like>> cells proliferate and differentiate into hepatocytes and biliary epithelial cells, and then repopulate the liver. In rodents, the so-called oval cells represent a heterogeneous cellular compartment in which well-defined subpopulations have yet to be isolated. In humans, the oval cell compartments may participate in repopulating the liver after acute massive necrosis, and has also been identified in chronic liver diseases (Roskams T, et al., Sell S et al.). As used herein, The phrase <<liver regeneration>> concerns the process by which <<stem-like>> cells proliferate and differentiate into hepatocytes and biliary epithelial cells, and then repopulate the liver as well as hepatocyte and biliary cells replication.

The term "Biologically active amounts" concerns the amount of the composition according to the invention sufficient for treating the liver diseases associated with a decreased number of hepatocytes, in which liver regeneration conduced by HIP/PAP can restore hepatic function.

Liver regeneration conduced by HIP/PAP can be useful in several situations such as surgery, transplantation, diseases, and after hepatotoxic compounds exposure conducing to liver necrosis or partial liver necrosis.

Firstly, the pharmaceutical compositions according to the invention are suitable in the treatment of acute and chronic liver failure.

Acute liver failure is generally caused by a massive apoptosis/necrosis of hepatocytes, and represents a devastating condition of viral or toxic origin. Acute liver failure is mainly induced by viral hepatitis (about 70% of cases), by drug poisoning, for example with acetaminophen during attempted suicide.

Chronic liver failure which can be treated by the compositions according to the invention, may be induced by hepatitis B or C virus infections or by alcohol. Chronic hepatitis B, cirrhosis, but also Non-alcoholic fatty liver disease (NAFLD). NAFLD is a term recently chosen to describe a clinical and pathological syndrome that spans a spectrum from simple steatosis to non-alcoholic steatohepatitis (NASH).

Accordingly, compositions according to the invention are suitable in the treatment of liver failure, consecutive to diseases such as: Hepatitis B, Hepatitis C, Urea Cycle defects, Familial hypercholesterolemia, Alcohol induced cirrhosis, Glycogen Storage Disease, Autoimmune Hepatitis, Primary Hyperoxaluria type I, Cryptogenic cirrhosis, CriglerNajjar syndrome type I, Congenital Hepatic Fibrosis, Neimaun-Pick Disease, Primary Biliary Cirrhosis, Familial Amyloidosis, Biliary Atresia, Hepatocellular Carcinoma, Primary Sclerosing Cholangitis, Hepatoblastoma, Alagille Syndrome, Hemangioendothelioma, Familial Cholestasis, Non-Carcinoid neuroendocrine tumor, Drug induced liver failure, benign liver tumor such as focal nodular hyperplasia Liver tumors such as Hepatocellular carcinoma and Cholangiocarcinoma, Acute/fulminant liver failure, Budd-Chiari syndrome, Alpha-I-antitrypsin deficiency, Wilson Disease, Hemochromatosis, Tyrosinemia, Protoporphyria, and Cystic fibrosis.

The compositions according to the invention are suitable in the treatment of all pathological situations resulting from an exposure to hepatotoxic compounds.

A number of hepatotoxic compounds, including alcohol, virus, such as HBV, HCV or HIV, mushrooms, such as phaloïde amanite, parasites such as *Plasmodium Falciparum*) or certain therapeutics, induce cytotoxicity and liver necrosis. Among these therapeutics, we can disclose anaesthetics, such as Enflurane, neuropsychotropics such as Hydrazides, anticonvulsants such as valproic acid, analgesics, such as Acetaminophen, antimicrobials such as Amphotericin B or Penicillin, hormones such as Acetohexamides, cardiovascular drugs, such as Papaverine, Immunosuppressives and anti-neoplastics, such as asparaginase, anti-hypertension drugs, anti-inflammatory drugs and miscellaneous drugs such as vitamin A, Oxyphenisatin, iodide Ion.

Although the exact mechanism of hepatotoxicity is uncertain, these compounds have deleterious effects on hepatocyte metabolism and contribute to the necrosis of hepatic tissue, and apparition of liver failure.

Especially, as shown in example 9, the pharmaceutical compositions according to the invention are suitable in the treatment of liver failure caused by acetaminophen, and have a preventive effect against acetaminophen intoxication.

A further object of the invention consists in a kit with limited adverse effect on liver necrosis comprising:
(i) a therapeutically effective amount of a hepatotoxic compound,
(ii) an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

The invention also encompasses a kit comprising a polypeptide fragment of HIP/PAP, biologically active portion of HIP/PAP or the entire HIP/PAP protein as defined above. The hepatotoxic compound of the composition can be one of those cited above.

The pharmaceutical compositions according to the invention are also suitable in the treatment of liver failure, consecutive to liver resection and liver transplantation. The pharmaceutical composition according to the invention can be administrated to the donor of a liver transplantation, to the receipt of such transplantation, to patients after a liver resection, in order to prevent the establishment or progress of liver failure by stimulating liver regeneration.

By stimulating liver regeneration, the compositions of the invention have other beneficial effects. Among them, we can cite the opportunity to make liver transplantation and partial liver transplantation with high effectiveness and also the opportunity to stimulate liver regeneration ex vivo, for example stimulate the growth of a liver transplant, liver epithelial cells, liver stem cells, or HIP/PAP genetically modified cells before transplantation.

Especially, the pharmaceutical compositions according to the invention can be formulated in a galenic form suitable for the preservation of liver transplants, preferably a liquid medium wherein HIP/PAP is dissolved or suspended.

The phrase "liver failure" is used herein in the broadest sense, and indicates any structural or functional injury resulting, directly or indirectly from a decreased number of liver epithelial cells i.e. hepatocytes and biliary cells.

The term "liver transplantation" has the common meaning in the art and includes partial and whole liver transplantation in which a liver of a donor is partially or wholly resected and partially or wholly transplanted into a recipient. Partial liver transplantation is classified by operation mode into orthotopic partial liver transplantation, heterotopic partial liver transplantation, and the like, and the present invention can be applied to any of them. In partial liver transplantation, a liver transplant or a partial liver transplant from a donor corresponding to about 30-50% of the normal liver volume of a recipient is typically transplanted as a graft into the recipient whose liver has been wholly resected. But the present invention has the effect of promoting liver regeneration or hepatocyte growth even if the graft is about 30% or less.

Partial liver transplantation is of particular importance, regarding the significant shortage of cadaveric organ donors, associated with an exponential growth in the number of patients on waiting lists worldwide and the success of living donor liver transplantation (LDLT) in paediatric recipients. In practice, the lack of cadaveric or size-matched liver grafts has led to the development of reduced, split, living-donor liver transplantation. Although regeneration occurs quickly in the transplanted graft, patients undergoing living donor liver grafts receive a smaller hepatic mass than those receiving a cadaveric transplant, and controversy over small-for size syndrome has escalated in recent years. Small-for-size liver grafts can be defined by a recognized clinical syndrome that results from the transplantation of an insufficiently large functional mass of liver in a designated recipient, and represents the greatest obstacle living donor transplantations in adults (Heaton, 2003). A graft to recipient body weight ratio of less than of 0.8 impairs venous inflows resulting in portal hypertension and enhanced metabolic demands in patients with in a poor clinical condition. The splitting of livers into right and left lobe grafts increases the potential risks of small-for-size in the recipient. These points is considered as a main factor causing small for size syndrome, which gives rise to impaired liver regeneration and necrosis of the small graft. As size mismatch is a major obstacle to adult living related liver transplantation, reduction of the impact of SFSS by using the pharmaceutical compositions above mentioned will optimise the use of available organs and reduce overall morbidity and mortality.

As used herein "liver transplant" means a liver transplanted into a recipient by the transplantation operation as described above, and also includes the so-called "partial liver transplant" corresponding to a graft consisting of the part of the liver of a donor. Liver transplantation means also injection of hepatocytes (genetically modified or stimulated to proliferate or differentiate) into portal vein.

As used in the case of liver transplantation, the phrase "liver regeneration" means morphologic changes in which lost liver tissues are replaced by hepatocyte growth of a liver transplant or partial liver transplant, but also includes biochemical changes such as improvement, recovery, or normalisation of hepatic functions. Specific subjects to be treated by the composition of the invention includes, for example patients who received partial liver transplant after the liver had been wholly resected for treating hepatic failure caused by liver diseases such as hepatitis, hepatic cirrhosis of alcoholic, viral, drug or unknown cause, or hepatic cancer.

The pharmaceutical compositions according to the invention are also suitable in the treatment of liver failure consecutive to Hepatic ischemia-reperfusion (I/R) which remains a significant limitation to both liver resection and liver transplantation, and may be responsible for liver failure, lung injury and death.

Although the following part of the specification relates especially to the formulation of compositions comprising the HIP/PAP protein, it is also suitable for therapeutic compositions comprising polypeptides fragments or biologically active portions of HIP/PAP.

For the purpose of the present invention, HIP/PAP can be formulated according to known methods to prepare pharmaceutically useful compositions, whereby HIP/PAP is combined in admixture with a pharmaceutically acceptable carrier. Suitable carriers and their formulations are described in Remington's Pharmaceutical Science, $16^{th}$ ed; 1980, Mack publishing Co, edited by Oslo et al.

By <<physiologically acceptable excipient>> is meant solid or liquid filler, diluent or substance, which may be safely used in systemic or topical administration. Depending on the particular route of administration, a variety of pharmaceutically acceptable carriers well known in the art include solid or liquid fillers, diluents, hydrotopes, surface active agents, and encapsulating substances.

These compositions will typically contain an effective amount of the HIP/PAP protein, for example, from on the order of about 6 µg/ml to about 10 mg/ml, together with a suitable amount of carrier to prepare pharmaceutically acceptable compositions suitable for effective administration to the patient.

HIP/PAP may be administered parenterally or by other methods that ensure its delivery to the bloodstream in an effective form. HIP/PAP may preferably be administered using an intra-hepatic route. Dosages and desired drug concentrations of such pharmaceutical compositions may vary depending on the particular use envisioned. A typical effective dose in mouse experiments is about 30 µg/kg. Interspecies scaling of dosages can be performed in a manner known in the art, e.g. as disclosed in Mordenti et al., Pharmaceut Res 8 p 1351 (1991).

The pH of the formulation depends mainly on the particular type and the concentration of HIP/PAP protein, but preferably ranges anywhere from about 3 to about 8.

Compositions particularly well suited for the clinical administration of HIP/PAP include sterile aqueous solutions or sterile hydratable powders such as lyophilised protein.

Typically, an appropriate amount of a pharmaceutically acceptable salt is also used in the formulation to render the formulation isotonic.

Sterility is readily accomplished by sterile filtration through (0.2 micron) membranes.

The HIP/PAP protein pharmaceutical composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutically <<effective amount>> of HIP/PAP protein to be administered will be governed by such considerations, and is the minimum amount necessary to induce, or alternatively enhance liver regeneration and prevent liver failure. Such amount is preferably below the amount that is toxic to the mammal or renders the mammal significantly more susceptible to infections.

The term <<administration>> or <<administered>> as used herein in reference to HIP/PAP protein refers to that administration of HIP/PAP protein which occurs prior to, simultaneous with, or after a liver resection, or a liver transplantation.

Cellular Compositions According to the Invention

An object of the invention is a composition comprising dividing hepatocytes in combination with a polypeptide comprising an amino acid sequence having 90% amino acid identity with the polypeptide consisting of the amino acid sequence starting at the amino acid residue 36 and ending at the amino acid residue 175 of sequence SEQ ID No 1.

Another object of the invention is a composition comprising hepatocytes that have been transfected with an expression cassette that drives the expression of a polypeptide comprising an amino acid sequence having 90% amino acid identity with the polypeptide consisting of the amino acid sequence starting at the amino acid residue 36 and ending at the amino acid residue 175 of sequence SEQ ID No 1.

An expression cassette that drives the expression of a polypeptide as described above can be obtained for example as described in the part entitled "Transgenic mice expressing HIP/PAP in the liver".

The hepatocytes as used herein, are directly collected from a liver, or obtained from stem cells and particularly from bone marrow stem cells that have been differentiated into hepatocytes. The differentiation of bone-marrow stem cells in hepatocytes has been reported by Petersen et al., (1999) and Mitchell et al. The recourse to such bone-marrow stem cells can avoid recourse to hepatectomy for obtaining in vitro hepatocytes cultures.

A further object of the invention is a composition comprising an effective amount of bone-marrow stem cells in combination with a polypeptide comprising an amino acid sequence having 90% amino acid identity with the polypeptide consisting of the amino acid sequence starting at the amino acid residue 36 and ending at the amino acid residue 175 of sequence SEQ ID No 1.

Without wishing to be bound to any particular theory, the inventors believe that the administration of bone marrow stem cells treated with HIP/PAP to a patient may accelerate the liver regeneration process.

The cellular compositions described above can be used for long-term in vitro culture of hepatocytes, for example for the purpose of in vitro cellular assays. The availability of the cellular compositions above avoid a recurrent recourse to hepatectomy for obtaining in vitro hepatocytes cultures. The invention also comprises pharmaceutical compositions for stimulating liver regeneration in vivo comprising an effective amount of a composition as defined here above.

In preferred embodiments of the present invention, the polypeptide from the compositions cited above is replaced by a polypeptide fragment of HIP/PAP, a biologically active portion of HIP/PAP or the entire HIP/PAP protein as defined in the present specification.

Process According to the Invention

Another object of the invention is a process for stimulating hepatocyte growth in vitro comprising:
(a) collecting hepatocytes;
(b) cultivating said hepatocytes in an appropriate culture medium;
(c) treating said hepatocytes with a mitogenic amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

By "mitogenic amount" it is meant that the hepatocytes will be treated with a sufficient amount of the polypeptide as defined herein before to induce hepatocytes growth when added into a culture of hepatocytes. Generally, a "mitogenic amount" as specified above consists of an amount of said polypeptide which induces proliferation of the cultured hepatocytes, as it can be easily determined by the one skilled in the art, for example through BrdU incorporation as disclosed in the examples.

Another object of the invention is a process for stimulating hepatocytes growth in vitro comprising:
(a) collecting hepatocytes;
(b) cultivating said hepatocytes in an appropriate culture medium;
(c) transfecting said hepatocytes with an expression cassette that drives the expression of the HIP/PAP protein in said hepatic cells.

Steps (a) to (c) can be conduced according to the techniques disclosed in example 5 and to the corresponding section in the part "material and methods".

The phrase "collecting hepatocytes", as used herein, means that hepatocytes are directly collected from a liver, or means that they are obtained from stem cells and particularly from bone marrow stem cells that have been differentiated into hepatocytes. The differentiation of bone-marrow stem cells in hepatocytes has been reported by Petersen et al., (1999) and Mitchell et al. The recourse to such bone-marrow stem cells can avoid recourse to hepatectomy for obtaining in vitro hepatocytes cultures. Thus, another object of the invention is a process for stimulating hepatocyte growth in vitro comprising:
(a) collecting bone marrow stem cells;
(b) cultivating said bone marrow stem cells in an appropriate culture medium;
(c) treating said bone marrow stem cells with a mitogenic amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

Without wishing to be bound to any particular theory, the inventors believe that the treatment described above enhances the bone marrow stem cells ability to regenerate the liver. In preferred embodiments of the present invention, the polypeptide from the process cited above is replaced by a polypeptide fragment of HIP/PAP, a biologically active portion of HIP/PAP or the entire HIP/PAP protein as defined in the present specification.

Use According to the Invention

Another object of the present invention consists of the use of a polypeptide comprising an amino acid sequence having 90% amino acid identity with the polypeptide consisting of the amino acid sequence starting at the amino acid residue 36 and ending at the amino acid residue 175 of sequence SEQ ID No 1 in the manufacture of a pharmaceutical composition for stimulating liver regeneration in vivo.

A further object of the present invention consists of the use of a polypeptide comprising an amino acid sequence having 90% amino acid identity with the polypeptide consisting of the amino acid sequence starting at the amino acid residue 36 and ending at the amino acid residue 175 of sequence SEQ ID No 1 in the manufacture of a pharmaceutical composition for the prevention of the establishment or progress of liver failure in a patient at risk for developing or having been diagnosed with liver failure.

The invention also encompasses the use of polypeptide fragments from HIP/PAP and biologically active portions of HIP/PAP as defined above.

In a preferred embodiment, the liver failure is a consequence of a liver resection, a liver transplantation, or hepatitis.

In a further aspect of the invention, the use according to the invention concerns a patient at risk for developing or having been diagnosed with a liver failure caused by a disease comprised in the group consisting of: Hepatitis B, Hepatitis C, Urea Cycle defects, Familial hypercholesterolemia, Alcohol induced cirrhosis, Glycogen Storage Disease, Autoimmune Hepatitis, Primary Hyperoxaluria type I, Cryptogenic cirrhosis, Crigler-Najjar syndrome type I, Congenital Hepatic Fibrosis, Neimann-Pick Disease, Primary Biliary Cirrhosis, Familial Amyloidosis, Biliary Atresia, Hepatocellular Carcinoma, Primary Sclerosing Cholangitis, Hepatoblastoma, Alagille Syndrome, Hemangioendothelioma, Familial Cholestasis, Non-Carcinoid neuroendocrine tumor, Drug induced liver failure, benign liver tumor such as focal nodular hyperplasia Liver tumors such as Hepatocellular carcinoma and Cholangiocarcinoma, Acute/fulminant liver failure, Budd-Chiari syndrome, Alpha-I-antitrypsin deficiency, Wilson Disease, Hemochromatosis, Tyrosinemia, Protoporphyria, and Cystic fibrosis.

Methods According to the Invention

Another object of the invention is a method for stimulating liver regeneration comprising administering an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1 to a patient.

In a preferred embodiment, the method according to the invention encompasses a method comprising administering an effective amount of polypeptides fragments from HIP/PAP, biologically active portions of HIP/PAP or the entire HIP/PAP protein as defined in the present specification.

Another object of the invention is a method for the treatment of a patient with a hepatotoxic therapeutic agent effective in the prevention or treatment of a disorder or pathologic physiological conditions, comprising:

(a) administering to said patient, simultaneously or in optional order, a biologically effective dose of said therapeutic agent and a preventatively effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

Another object of the invention is a method for the prevention of the establishment or progress of liver failure, consequence of a liver resection, a liver transplantation, or a hepatitis comprising administering to a patient an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

According to the method above, the polypeptide is administrated before, during or after a liver resection or a liver transplantation. The polypeptide can also be administrated to the donor of a liver transplantation, or to the receipt, in order to avoid for example post-surgery complications. According to the method above the polypeptide used is a fragment of HIP/PAP, a biologically active portion of HIP/PAP or the entire HIP/PAP protein as defined in the present specification.

Another object of the invention is a method for stimulating liver regeneration in a patient comprising:

(a) collecting hepatocytes from said patient;
(b) cultivate said hepatocytes in an appropriate culture medium;
(c) treating said hepatocytes with a mitogenic amount of a polypeptide comprising an amino acid sequence having 90% amino acid identity with the polypeptide consisting of the amino acid sequence starting at the amino acid residue 36 and ending at the amino acid residue 175 of sequence SEQ ID No 1; and
(d) injecting said cells into said patient.

By "mitogenic amount" it is meant that the hepatocytes will be treated with a sufficient amount of the polypeptide as defined herein before to induce a liver regeneration when injected in a patient. Generally, a "mitogenic amount" as specified above consists of an amount of said polypeptide which induces proliferation of the cultured hepatocytes, as it can be easily determined by the one skilled in the art, for example through BrdU incorporation as disclosed in the examples.

Steps (a) to (d) can be conduced according to the techniques disclosed in example 5 and to the corresponding section in the part "material and methods". In a preferred embodiment, the method comprises additional steps:

(e) monitoring said patient for indication of liver failure, and
(f) Continuing injections according to step (d) until said liver regeneration is sufficient.

Another object of the invention is a method for stimulating liver regeneration in a patient comprising:

(a) collecting hepatocytes from said patient;
(b) cultivate said hepatocytes in an appropriate culture medium;
(c) transfecting said hepatocytes with an expression cassette that drives the expression of the HIP/PAP protein in said hepatic cells, and
(d) injecting said cells into said patient.

An expression cassette that drives the expression of a polypeptide as described above can be obtained for example as described in the part entitled "Transgenic mice expressing HIP/PAP in the liver".

A further object of the invention is a method for stimulating liver regeneration in a patient comprising:
(a) collecting bone marrow stem cells from said patient;
(b) cultivating said bone marrow stem cells in an appropriate culture medium
(c) treating said cells with a mitogenic amount of a polypeptide comprising an amino acid sequence having 90% amino acid identity with the polypeptide consisting of the amino acid sequence starting at the amino acid residue 36 and ending at the amino acid residue 175 of sequence SEQ ID No 1
(d) injecting the cells obtained at step (c) into said patient.

The availability of the method above avoid a recurrent recourse to hepatectomy for obtaining in vitro hepatocytes cultures. Without wishing to be bound to any particular theory, the inventors believe that the administration of bone marrow stem cells treated with HIP/PAP to a patient may accelerate the liver regeneration process.

Steps (a) to (d) can be conduced according to the techniques disclosed in example 5 and to the corresponding section in the part "material and methods". In a preferred embodiment, the method comprises additional steps:
(e) Monitoring said patient for indication of liver failure, and
(f) Continuing injections according to step (e) until said liver regeneration is sufficient.

In another embodiment, the invention relates to a method for the prevention of the establishment or progress of liver failure in a patient at risk for developing or having been diagnosed with viral or autoimmune hepatitis, or a cirrhosis comprising administering to said patient a liver failure preventative amount of a polypeptide comprising an amino acid sequence having 90% amino acid identity with the polypeptide consisting of the amino acid sequence starting at the amino acid residue 36 and ending at the amino acid residue 175 of sequence SEQ ID No 1.

In another embodiment of the method above, the polypeptide used, is a fragment of HIP/PAP, a biologically active portion of HIP/PAP or the entire HIP/PAP protein as defined in the present specification.

The invention also concerns HIP/PAP, as an active ingredient of a composition for stimulating liver regeneration in vivo, comprising an effective amount of a polypeptide comprising an amino acid sequence having 90% amino acid identity with the polypeptide consisting of the amino acid sequence starting at the amino acid residue 36 and ending at the amino acid residue 175 of sequence SEQ ID No 1 in combination with at least one physiologically acceptable excipient.

Further details of the invention are illustrated in the following non-limiting examples.

Materials and Methods

HIP/PAP Production and Purification:

HIP/PAP was produced in transgenic mouse milk carrying the rabbit WAP gene able to drive expression of the HIP/PAP gene in the mammary gland, as previously described by the inventors (Christa et al., 2000).
Transgenic mice carrying the WAP/HIP construct were generated by microinjection into one-cell mouse zygotes of C57Bl/6×CBA hybrid strains. They were identified by tail DNA analysis on Southern blots. Mouse DNA was digested with SacI, and the generated fragments were separated on 1% agarose gels and transferred to Nytran 13N. The presence of the transgene was detected using a 4.4-kb XhoI fragment derived from the upstream region of the rabbit WAP gene.

All experiments, including animal welfare and conditions for animal handling before slaughter, were conducted in accordance with French Ministry of Agriculture guidelines (dated 19 Apr. 1988).

Milk Samples

Milk was collected at day 13 postparturition from anaesthetised mice previously injected with 0.05 U of oxytocin to stimulate milk letdown. Mouse milk was diluted (1/10) in 10 mM Tris/HCl pH 7.5, 100 mM $CaCl_2$, and centrifuged for 30 min at 40 000 g. The pellet was discarded and the supernatant was spun again under the same conditions. The supernatant or lactoserum was used immediately for the purification of HIP/PAP or kept frozen at 20° C.

Purification of HIP/PAP Protein from Transgenic Mouse Milk

The resulting lactoserum (see above) was acidified to pH 4.6 by the addition of acetic acid (1 M) under stirring at 0° C. for 30 min. The precipitated material was removed by centrifugation at 110 000 g for 1 h in a Beckman 50.2 Ti rotor (Gagny, France). The supernatant was dialysed overnight at 4° C. against 1 L of 20 mM sodium acetate buffer pH 4.8, clarified by high speed centrifugation as above and filtered on a Millex 0.22 µm filter (Millipore, Guyancourt, France) before loading onto a Mono S HR 5/5 cation-exchange column previously equilibrated with 70 mM sodium acetate buffer pH 4.8. The flowthrough was discarded, and a 20-mL gradient of 0-500 mM NaCl in the working buffer was started when the absorbance returned to baseline. The column flow rate was 1 mL·$min^1$, and 1-mL fractions were collected. HIP/PAP-containing fractions were pooled, diluted in 5 vol. of 140 mM sodium acetate buffer at pH 4.0 and reapplied to the Mono S HR 5/5 column equilibrated with 140 mM sodium acetate buffer pH 4.0. The flowthrough was discarded and the column was developed with a 20-mL gradient ranging from 0 to 400 mM NaCl in the working buffer. The column flow rate was 1 mL/min and 1-mL fractions were collected. Fractions containing HIP/PAP were pooled, diluted in 1 vol. of glycerol and stored at 20° C.

Protein concentrations in the samples were determined using the Peterson protein assay. Denaturing polyacrylamide gels in sodium dodecyl sulfate (12.5% acrylamide, SDS/PAGE) were performed according to Laemmli. Coomassie blue staining gels were scanned and quantified using an imagemaster.

Animals

Transgenic Mice Expressing HIP/PAP in the Liver.

Figure 1:
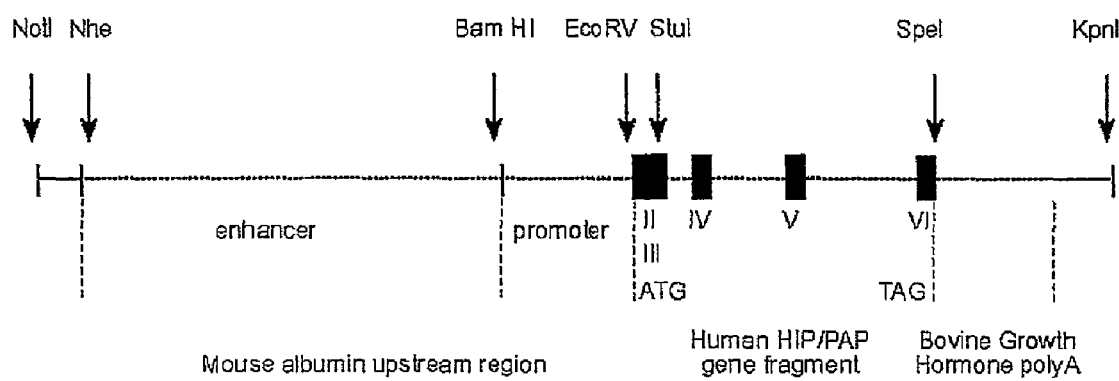
FIG. 1 Schematic representation of the transgene.

The regulatory region of the mice albumin gene 18 was cloned upstream the HIP/PAP gene fragment to drive a human HIP/PAP gene expression specifically in the liver as described in the FIG. 1. The entire NotI/KpnI-linearized construct was microinjected into single cell mouse zygotes of hybrid strains in the Experimentation on the Transgenesis department (Villejuif France). The 24 and 27 homozygous transgenic lines were developed from independent founders on genetic background. Animal welfare, conditions for animal handling before slaughter and all experimental procedures were ensured in line with the French Ministry of Agriculture guidelines (dated 19, Apr. 1988).

Control Mice

C57BL/6 mice were provided by IFFA CREDO (L'Arbresle, France) and were used as controls of HIP/PAP transgenic mice.

Recipients of Isolated Hepatocytes

Six-week-old female severe combined immunodeficient (SCID) mice (IFFA-CREDO, L'Arbresle France) were used as the recipients of hepatocytes isolated from male HIP/PAP transgenic mice or male C57BL/6 mice (IFFA-CREDO, L'Arbresle France), to minimize any risk of cell rejection.

Partial Hepatectomy and BrdU Incorporation in vivo.

Liver resection represents 70% of the total liver mass, as described by Higgins and Anderson (Higgins et al.) in two month old mice. Animals received one intra-peritoneal injection of 60 mg per kg body weight BrdU in 0.9% NaCl for 2 hours before dissection. They were sacrificed 24, 36, 46 and 55 hours post-hepatectomy. Animals and livers were weighted and BrdU-labelled nuclei were scored after incubation with anti-BrdU antibody (clone Bu 20A) and revelation was performed using the Universal LSAB2 horseradish peroxydase kit (Dako) with at least 20 low magnification (×10) microscope fields for each liver slide (Olympus BX60). More than 1600 nuclei were screened per slide.

Hepatocytes in Primary Culture

Primary mouse hepatocytes were isolated from 2 to 3 months old mice, as previously described (Klaunig at al, Renton et al) with Liberase Blendzyme. Viable hepatocytes were purified using a low speed iso-density Percoll centrifugation method, as described by (Kreamer et al). Cells were resuspended in 199 medium containing penicillin, streptomycin, fungizone, bovine serum albumin (0.1%) and fetal calf serum (10%), at densities of $2 \times 10^5$ and $4 \times 10^5$ for proliferation and apoptotic experiments respectively in Primaria plates. Cells were maintained at 37° C. in a humidified atmosphere and the medium was changed after attachment to the plates for 2 and 3 hours. Following attachment, the cells were rinsed once and cultured with the same medium containing no serum and then exposed to ActD (0.05 µg·ml$^{-1}$) plus TNF-α at ranges of concentration from 0.2 to 40 ng/ml for 17 to 18 hours, unless otherwise specified in the figure legends. For proliferation experiments, the medium was supplemented with 3,5,3'-triiodothyronine 5 $10^{-8}$ M, dexamethasone $10^{-7}$ M, Insulin 10 µg/ml 2 $10^{-6}$ M, transferrin 5.5 µg ml, selenium 7 ng/ml, pyruvate 20 mM and foetal calf serum 5%.

DNA Synthesis in Primary Culture Hepatocytes

To measure DNA synthesis, BrdU (20 mM) was added for the last 16 hours prior to evaluation. The hepatocytes were washed with PBS, fixed, and rendered permeable in 30:70 acetic acid/ethanol solution at −20° C. for 30 minutes. Incorporated BrdU was localised using the BrdU Labelling and Detection kit II. Replicative DNA synthesis was measured by scoring the percentage of BrdU labelled cells in at least 10 low magnification microscope field for each sample (Olympus CK2). More than 1000 hepatocytes were screened per well.

Cell Viability and Evaluation of Apoptosis in Primary Culture Hepatocytes.

Seventeen hours after the addition of TNF-α, the monolayer was fixed with 4% paraformaldehyde for 20 minutes at room temperature, stained with Hoechst 33258 (0.5 µg/ml). Apoptotic cells were examined at wavelengths between 350 and 460nm using an Olympus BX60 inverted fluorescence microscope (Olympus America Inc.). Loss of cell viability was quantified using the MTT assay: 30,000 cells per well in a 96 well microtiter plate were treated with x µl (0.5 mg/ml) MTT solution, freshly dissolved in medium for 1 hour at 37° C. The medium was then aspirated and 100 µl DMSO were added to solubilize the dye. Absorbance was measured at 570 nm using a Dynex MRX 96 well microplate reader (Dynex Technologies, France). Each measurement was performed in quadruplicate, for HIP/PAP and wild type hepatocytes dispensed on the same plate. Percentage cell survival was calculated by taking the optical density reading of cells receiving a particular treatment, dividing that number by the OD reading for untreated, control cells and then multiplying by 100. Comparison of the results with the number of apoptotic cells visualised using Hoechst 33258 validated the accuracy of the MTT assay.

Liver Cell Isolation and Transplantation

Hepatocytes were isolated from two-month old male HIP/PAP transgenic mice and male C57BL/6 mice, using the Liberase Blendzyme, as previously described by Klaunig and Renton. Viable hepatocytes were purified using a low-speed, iso-density Percoll centrifugation method, as described by Kreamer. Female SCID mice were anesthetized with xylazine (Bayer, Leverkusen, Germany) and ketamine (Biomérieux, Lyon France) dissolved in NaCl 0.9%, spleens were exteriorized through a small, left-flank incision, and a syringe with a 26-gauge needle was used to inject 100 µl of cell suspension ($0.75 \times 10^6$ viable hepatocytes) in Willliams medium (Gibco/BRL). Recipient SCID was held for 30 days to allow sufficient time for the proliferation and reorganization of donor hepatocytes into the liver parenchyma, before partial hepatectomy was performed.

Evaluation of Liver Regeneration.

Animals received one intra-peritoneal injection of 60 mg kg$^{-1}$ body weight BrdU in 0.9% NaCl 2 hours before dissection. They were sacrificed 24, 36, 46 and 55 hours post-hepatectomy. Animals and livers were weighted and BrdU-labelled nuclei were scored after incubation with anti-BrdU antibody (clone Bu 20A) and revelation was performed using the Universal LSAB2 horseradish peroxydase kit (Dako,) with at least 20 low-magnification (×10) microscope fields for each liver slide (Olympus BX60). More than 1600 nuclei were screened per slide.

HIP/PAP Purified Protein Injection after Hepatectomy.

Recombinant HIP/PAP protein was produced and purified as previously described (Christa et al., 2000), and was diluted in NaCl 0.9% at 6 µg/ml. 100 µl HIP/PAP protein or PBS (Phosphate Buffered Saline) was injected into the spleens of Severe Cellular ImmunoDeficient (SCID) mice 36 h after partial hepatectomy. The animals were killed 8 days after partial hepatectomy.

Detection of Transplanted Liver Cells by RT-PCR Analysis.

RNA from frozen liver tissues was extracted according to TRIZOL reagent (Life Technologies) supplied instructions. CDNA was synthesised by 200 units Moloney murine leukaemia reverse transcriptase (Promega) and primed with 400 ng random primers (Invitrogen), from 1 µg total RNA, at 42° C. for 45 min, in the presence of 10 U RNasin, 1× buffer supplied by the enzyme, 40 mmol l$^{-1}$ of the four deoxynucleotides. PCR was performed with 40 amplification cycles of 1 min each at the following temperatures: 94° C., 60° C., and 72° C., from 1/8 cDNA, by using pure Taq™ Ready-To-Go™ PCR Beads (Amersham Biosciences). Human HIP/PAP transgene expression was detected with primers 19/101. Endogenous HIP/PAP/Mo gene expression was detected with 104/105 primers which from the mouse published sequence of Itoh and Terakoa ( ).

19 sens: 5' cgc ccc ggg atg ctg cct ccc atg gcc ctg 101 antisens: 5' cgc gaa tcc gcc cat gat gag ttg cac acc aaa c 3'

104 sens: 5' cgc gga ttc atg ctg cct cca aca gcc tgc t 3'

105 antisens: 5' cgc aag ctt tta acc agt aaa ttt gca gac ata 3'

HIP/PAP Assays: Western Blot Analysis, Immunohistochemistry and ELISA Test.

HIP/PAP protein was produced and purified from the milk of lactating transgenic mice as described above, and according to Christa et al., 2000. Western blot analysis and immunohistochemistry were performed with pre-HIP antibodies, as previously described (Christa et al., 1999). Serum HIP/PAP levels were assayed using a sandwich ELISA test, in accordance with the manufacturer's instructions (Dynabio, La Gaude, France).

Activation of the Transcription Factor STAT3

Activation of the transcription factor STAT3 was studied by the TramsAM kit (Active motif) and by Western blot analysis performed as previously described (Simon et al., 2003), with total anti-STAT3 and anti-phospho STAT3 antibodies (Santa Cruz)

Liver Cytokines Expression

Liver cytokines expression were evaluated by RNase protection assay as previously described (Tralhao J G, 2002)

APAP Intoxication:

HIP/PAP transgenic mice and C57Bl6 was intoxicated by a lethal dose of APAP (1000 mg/kg), as described by Bedda et al., 2003 or Ferret P. J. et al., 2001. Recombinant HIP/PAP protein (600 ng or 1200 ng) was intravenous injected 1 hour before intraperitoneal injection APAP to C57Bl6 mice. The animals were monitored for 24 hours, and survival was calculated using the Kaplan-Meier method.

Statistical Analyses.

Results for hepatocytes in primary culture were expressed as mean+/−SD, and statistical significance ($P<0.05$) was determined using an unpaired Student's test. In vivo liver regeneration was represented by the percentages of nuclei incorporating BrdU using the box and whiskers representation, and the statistical significance of differences between HIP/PAP transgenic and wild-type mice was determined by the Mann-Whitney U-test ($P<0.05$), because the data distribution was not normal (Statview 5', Abacus Concepts, Berkeley, Calif.).

Results

EXAMPLE 1

Characterization of Human HIP/PAP Transgenic Mice

The HIP/PAP transgene was specifically expressed in the liver, and HIP/PAP-expressing mice did not develop livers tumours, after a two year following. Immunohistolocalization analysis detected HIP/PAP protein in the liver of transgenic mice as diffuse intra-hepatocyte immunostaining, occupying most of the cytoplasm of the hepatocytes (FIGS. 2A, 1 and 2). Staining was heterogenous and positive regions were located either in centrolobular or portal areas of the liver acinus. This heterogeneous distribution likely reflects HIP/PAP secretion, thus hepatocytes could be either positive or negative before or after HIP/PAP secretion respectively. HIP/PAP protein was secreted into the serum (250 ng/ml to 700 ng/ml) in homozygote transgenic lines 24 and 27, and into the culture medium of primary hepatocytes (30 to 120 ng/ml per $2.10^5$ cells). No difference in morphology and ploïdy was detected between HIP/PAP-expressing and control hepatocytes by histological examination (mouse hepatocytes were 80% binuclear after adhesion as previously described by Leist et al.). HIP/PAP immunohistochemistry views of hepatocytes in culture showed that more than 50% of the hepatocytes were HIP/PAP labelled (FIGS. 2A, 3 and 4). Western-blot analysis detected HIP/PAP as a 16 kDa protein in liver extracts and primary culture hepatocytes from HIP/PAP transgenic mice (FIG. 2B). HIP/PAP protein was not detected in wild type mice. Actin hybridization allowed an accurate estimation of the 50 μg protein loaded for livers and hepatocytes (50 μg corresponded approximately to 50,000 hepatocytes).

EXAMPLE 2

Liver Regeneration is Stimulated in Mice Expressing the Human HIP/PAP Gene

To test in vivo the HIP/PAP effect on liver cell proliferation, liver regeneration induced by partial hepatectomy was examined. Low magnification (×20) views for times 24, 36, 46 and 55 hours post partial hepatectomy are presented FIG. 3A. At the indicated times, percentages of positive BrdU cells were higher in HIP/PAP transgenic than in wild-type livers, despite the low overall frequency of nuclei which had incorporated BrdU in both groups. The percentages of nuclei incorporating BrdU were significantly higher in HIP/PAP transgenic mice (median 33%; range 20-42%) compared to wild-type (median 18%; range 11-27%) ($P=0.0014$), 46 hours after partial hepatectomy (FIG. 3 B). To reinforce the hypothesis that HIP/PAP protein may act as Growth Factor during liver regeneration, the time-course of the hepatic mass restoration in wild-type and transgenic mice was established, after hepatectomy (FIG. 3C). Animal and liver weights were measured in normal non hepatectomized mice. The liver/body ratio of weight was calculated and expressed as the average percentage ±SD. There was no difference in this ratio between the two groups: 0.0460±0.0064, n=12 and 0.0489±0.0035 n=16 for wild-type and HIP/PAP transgenic mice, respectively. Liver recovery was higher in the HIP/PAP transgenic than in wild-type mice, and the difference was statistically significant at 48 hours ($p<0.001$), 60 hours ($p<0.003$) and 96 hours ($p<0.002$). At 120 hours, the liver weight recovered to the same percentage in both wild-type and HIP/PAP transgenic mice.

EXAMPLE 3

HIP/PAP Mitogenic Effect in Primary Culture Hepatocytes

In order to further investigate the enhanced liver regeneration observed in vivo after hepatectomy in HIP/PAP transgenic mice, primary cultures of hepatocytes were used to evaluate a HIP/PAP mitogenic effect. Hepatocytes derived from HIP/PAP transgenic and wild-type mice exhibited two peaks DNA synthesis, 60 and 84 hours after plating, when stimulated by EGF (FIGS. 4 A and B). At 60 hours, mean percentages of BrdU-positive hepatocytes were 31±7% (n=19) and 16±4% (n=20) in transgenic and wild-type mice, respectively ($p<0.0001$). When cells were stimulated by HGF, DNA synthesis was also higher in HIP/PAP than in wild-type hepatocytes (41±14% n=4, versus 31±11%, n=4, respectively after 60 hours) although this difference did not attain significance. When hepatocytes were not stimulated by Growth Factor, BrdU incorporation were 11%±3 (n=8) and 6%±3 (n=7) in transgenic and wild-type hepatocytes respectively and the difference was statistically significant (p=0.0146). HIP/PAP is a secreted protein, and it was therefore tested whether it might act as a paracrine mitogenic factor. When HIP/PAP protein (40 ng·ml$^{-1}$) was added to wild-type hepatocytes, EGF-induced DNA synthesis increased from 16±4% to 24±7% (p=0.0168; n=8; FIG. 4C). These results showed that HIP/PAP was a mitogenic factor for hepatocytes in primary culture. The mitogenic effect of HIP/PAP on hepatocyte proliferation was thus demonstrated both in vivo and in vitro.

EXAMPLE 4

HIP/PAP Anti-apoptotic Effect Against Apoptosis Induced by TNF-α+ActD in Primary Culture Hepatocytes It was next examined whether the HIP/PAP mitogenic effect was associated with a HIP/PAP antiapoptotic effect. Rat hepatocytes in primary cultures were not sensitive to cell death caused by TNF-α treatment alone. Instead, they die through apoptosis after exposure to TNF-α combined with a low dose of ActD (22). Mouse hepatocyte cell death was induced by TNF-α combined with an ActD dose as low as 0.05 μg/ml, despite ActD (0.05 μg ml$^{-1}$) alone did not induce any loss of viability (FIG. 5B). It is shown (FIG. 5A) that hepatocytes expressing HIP/PAP resisted TNF-α+ActD-induced apoptosis after a 16-17 hours of treatment. Cell survival reached 75% versus 43% (p<0.0001) for 2 ng ml$^{-1}$ TNF-α, and 60% versus 27% for 20 ng ml$^{-1}$ TNF-α, (p<0.0001). The LD$_{50}$ for TNF-α was over 40 ng ml$^{-1}$ and 1 ng ml$^{-1}$ in HIP/PAP and wild-type hepatocytes, respectively. Pre-treatment of cells with pan-anticaspase z-VAD-fmk (50 μM) completely prevented TNF-α-induced cell death, thus indicating that this process occurs via hepatocyte apoptosis. It was also examined whether dying cells exhibited the typical features of apoptosis. When stained with Hoechst 33258, non-viable cells displayed condensed chromatin, fragmented nuclei and apoptotic bodies, whereas viable cells did not. The features of apoptotic bodies were organized in "rosettes" characteristic of the hepatocyte apoptosis induced by TNF-α (FIG. 5C). When HIP/PAP protein (40 ng ml$^{-1}$) was added to wild-type hepatocytes, protection against 20 ng ml$^{-1}$ TNF-α+ActD rose from 27% to 47% (p<0.0001). These data demonstrate that HIP/PAP partly abrogated TNF-α-induced apoptosis in primary hepatocytes.

EXAMPLE 5

Liver Regeneration is Stimulated in Mice by Hepatocytes Isolated from HIP/PAP Transgenic Mice An in vivo experimental model was set up to test for the effect on overall liver regeneration of HIP/PAP expression in a minority of liver cells. Liver cell transplantation of hepatocytes isolated from HIP/PAP transgenic and C57BL/6 mice was thus performed, and then the extent of liver regeneration after partial hepatectomy was tested in the SCID recipient mice.

Two complementary approaches were used to assess liver cell transplantation. First, advantage of the human HIP/PAP transgene expression was took to monitor the fate of transplanted liver cells, by using immunohistochemistry with HIP/PAP antibodies. A semi quantitative estimation indicated that transplanted cells constituted less than 1/1000 in the recipient livers. Moreover, HIP/PAP expression was shown in a limited number of liver cells without preferential distribution in the liver sections (portal or centrolobular area). Second, it was took advantage of the presence of the human HIP/PAP sequence to perform RT-PCR. Human HIP/PAP expression was indeed detected in recipient SCID liver, before partial hepatectomy, thus confirming liver cell transplantation Moreover; human HIP/PAP expression persists in the liver section obtained at different times after hepatectomy. These results demonstrated that transplanted cells persisted upon stimulation of recipient liver regeneration and retained gene expression.

The effects of the intrahepatic implantation of liver cells concerning the extent of liver regeneration after partial hepatectomy were then assessed. Macroscopic evaluation of the liver 8 days after partial hepatectomy showed a marked increase in liver mass recipient mice transplanted with liver cells from transgenic HIP/PAP mice (FIG. 6A). Moreover, these findings were confirmed by liver weight measurements, which were significantly higher in recipient mice transplanted with liver cells from transgenic HIP/PAP (FIG. 6B). BrdU incorporation analysis performed 48 h after partial hepatectomy did confirm a marked increase in cellular DNA synthesis upon transplantation of human HIP/PAP-expressing hepatocytes. Thus the transplantation of 750 000 viable hepatocytes was sufficient to increase liver regeneration. Standard histological examination of the liver did not reveal any obvious morphological changes.

EXAMPLE 6

Liver Regeneration is Stimulated in Mice by Administration of HIP/PAP

It was tested whether the injection of purified HIP/PAP might have the same effect as transplantation on liver regeneration. The weights of remnant livers were compared 8 days after partial hepatectomy in SCID mice that had been injected 36 h after partial hepatectomy with 100 μl of purified HIP/PAP (600 ng per mice). The results presented on FIG. 7 indicated a 10% increasing of liver weight in mice injected with HIP/PAP compared with that seen in mice injected with PBS. This observation demonstrated a mitogenic paracrine effect of HIP/PAP protein in vivo.

EXAMPLE 7

Liver Regeneration and Mitose are Stimulated in C57Bl6 Mice by Administration of HIP/PAP The effect of the HIP/PAP protein versus saline injected immediately after partial hepatectomy of C57Bl6, on the restoration of the hepatic mass, the incorporation of BrdU and mitosis, 46 hours after partial hepatectomy, has been compared. (FIG. 8). An increase in the restoration of the liver mass was observed 46 hours after partial hepatectomy, although the difference was not statistically significant (p=0.08) probably because 46 hours is too early to observe a consistent increase in liver mass. However, there are an increase in BrdU incorporation (p<0.02) and number of mitosis (p<0.04) in HIP/PAP injected mice.

Distributions of incorporation of BrdU and mitosis were heterogenous, as assessed by the differences in means and medians in each group of mice. By using the median test (which is an application of the Ficher exact test), it has been validated that mice injected with HIP/PAP represented a group statistically different from mice injected with NaCl. (Table I)

TABLE I

|   | BrDU positive nuclei (%) | | | Mitotic hepatocytes (%) | | |
| --- | --- | --- | --- | --- | --- | --- |
| n | NaCl 16 | HIP 15 | combined 31 | NaCl 16 | HIP 15 | combined 31 |
| mean | 12.669 | 22.313 | 17.335 | 0.525 | 1.567 | 1.029 |
| median | 7.300 | 23.000 | 15.800 | 0.000 | 0.7200 | 0.000 |
| P-value | | | 0.0038 | | | 0.0113 |

To characterize the benefit of HIP/PAP on liver regeneration, the model of the median test has been used to classify the mice in four nominal groups according to the combined median for BrdU and mitosis. (FIG. 9). Statistical analysis of mice populations according to BrdU associated to mitosis has shown that more HIP/PAP-injected mice were positive for both BrdU nuclei and mitotic hepatocytes (liver in S/M phase of the cell cycle) than saline-injected mice (p=0.01), suggesting that HIP/PAP could accelerate hepatocyte progression through the cell cycle.

EXAMPLE 8

Expression of Liver Cytokines and Activation of the STAT3 Transcription Factor During the Time Course of Liver Regeneration Liver regeneration has to be primed by TNF-α and IL-6 cytokines in order to initiate the hepatocytes to enter the G1 phase of the cell cycle. Under control of IL-6, the STAT3 transcription factor is phosphorylated-activated and translocated to the nucleus. However, the persistence of TNF-α/IL6 expression and STAT3 activation is deleterious and delays the time-course of regeneration. the effect of HIP/PAP on liver cytokine expression and on the activation of STAT3 has been investigated. In this context, cytokine expression in the liver at T0 of PHX (partial hepatectomy) and after 46 hours of SCID mice transplanted with HIP/PAP versus control hepatocytes has been compared. Rnase protection methodology allowed to compare in the same experiment lymphotoxin-β (LTβ), TNF-α and TGF-β in a pool of 4 liver extracts (FIG. 10; HIP/PAP transgenic mice lanes a and b; SCID mice lanes c and d) at T0 (lanes a and c) and at T46 hours post PHX (lanes b and d). Densitometric analysis quantified the signals which have been normalized versus two house keeping genes (L32 and GAPDH). The results showed no difference in the hepatic expression of TGF-β when transplantation was done with HIP/PAP or control hepatocytes: at 46 hours post PHX, TGF-β increased at the same extent. On the contrary, the expression of LTβ and TNF-α (both cytokines belongs to the same functional family) was inhibited in the SCID livers transplanted with HIP/PAP hepatocytes. These results show that HIP/PAP inhibits hepatic TNF-α expression in SCID liver.

Rnase protection methodology did not allow detecting IL6 expression during the liver regeneration of the SCID. However, the kinetic of activation of the transcription factor STAT3 has been investigated in HIP/PAP transgenic and C57Bl6 mice. The accumulation/degradation time course of nuclear phospho-STAT3 was activated in HIP/PAP transgenic versus C57Bl6 mice, during the first 24 hours after PHX (FIG. 11). Activation was detected as soon as 1 hour post PHX in HIP/PAP but not in C57Bl6 mice (p=0.02). Moreover, STAT3 activation was back to lower levels in HIP/PAP than in C57Bl6 mice (p=0.04), as soon as 12 hours. The results were validated and visualized by western blot analysis with anti-STAT3 phosphorylated antibodies. (FIG. 11)

EXAMPLE 9

HIP/PAP is a Protective Drug Against APAP-induced Acute Liver Failure

The induction of human acute liver failure could be mimicked by a relevant experimental animal model, consisting of APAP (acetaminophen) intoxication. APAP overdose leads to the increased production of NAPQ1, a highly reactive metabolite that depletes the intracellular pool of GSH, a non-protein thiol with both oxidant scavenger and redox regulating capacities. Consequently, during APAP intoxication in the mouse, toxic reactive oxygen species (ROS) are generated leading to acute liver failure. A large single dose of APAP in the mouse, as in humans, can cause massive centrolobular parenchymatous destruction and hepatocyte death. The therapeutic activity of HIP/PAP protein in a mouse model of APAP-induced acute liver failure has been investigated. For this purpose, the resistance of HIP/PAP transgenic mice against a lethal dose of APAP injected in wild-type mice has been tested. Drug-induced acute liver failure was achieved in 24 HIP/PAP transgenic and 24 C57/bl6 mice (12 males and 12 females in each group) by the intraperitoneal injection of a lethal dose of 1000 mg/ml ($APAP_{1000}$) diluted in 200 μL sterile phosphate buffer saline.

The survival times showed that 80% of HIP/PAP transgenic mice (males or females) survived for more than 24 hours, versus 25% in the wild-type control group. These results show that HIP/PAP protein is a good candidate for clinical therapeutic applications aimed at preventing and treating liver failure, through its action on both the regenerative and live status of liver cells (FIG. 12).

To investigate the preventive paracrine protection of HIP/PAP protein against APAP intoxication, HIP/PAP protein has been injected by intravenous in the tail of C57Bl6 1 hour before APAP. The results showed a dose dependent preventive protection of HIP/PAP protein: for 600 ng, 4/10 and 2/10 HIP/PAP-injected and saline-injected mice survived respectively; for 1200 ng, 8/10 and 2/10 HIP/PAP-injected and saline-injected mice survived, respectively.

EXAMPLE 10

HIP/PAP Protein Exhibits No Toxic Effects During the Long-term in vivo Follow-up of HIP/PAP-expressing Transgenic Mice Any drug capable of stimulating liver cell proliferation has a potential to induce cancer, so that the risks of developing HCC must be determined prior to any administration. Two models of transgenic mice expressing human HIP/PAP gene under either the promoter of the mouse albumin gene (two strains) or the promoter of the mouse metallothioneine gene (two strains) have been developed. Both models target HIP/PAP gene expression in the liver and secretion of the HIP/PAP protein in the blood. None of the HIP/PAP-expressing mice had developed liver (or other) tumours, after a two-year follow-up period.

EXAMPLE 11

HIP/PAP Delays HCC Development in Predisposed Transgenic Mice

The effects of HIP/PAP protein on a model of liver carcinogenesis from the long-term follow-up of bi-transgenic mice has been investigated. The HIP/PAP transgenic mice (metallothionéine promoter) were crossed with WHV/c-myc mice in which the liver-specific expression of c-myc driven by woodchuck hepatitis (WHV) regulatory sequences causes liver cancer in all animals Terradillos et al. (1997). Survival curves showed that the T50 of bitransgenic mice was 60 weeks (n=87 mice) versus 42 weeks for the T50 of WHV/c-myc oncomice (n=39 mice), which was the median published by Terradillos et al. (1997). Survival curves were identical for HIP/PAP transgenic mice and for littermate negative controls. Thus, firstly, toxicity of HIP/PAP protein during the lifespan of these mice has not been detected, and secondly, it has been shown that HCC onset is delayed in mice carrying both transgenes, i.e. WHV/c-myc and HIP/PAP. (FIG. 13)

There is no evidence for toxicity during the long-term administration of HIP/PAP. Moreover, a delayed onset of HCC in c-myc-induced liver cancer transgenic mice has been observed.

References:

Abergel C, Chenivesse S, Stinnakre M G, Guasco S, Brechot C, Clayerie J M, Devinoy E, Christa L. (1999) Crystallization and preliminary crystallographic study of HIP/PAP, a human C-lectin overexpressed in primary liver cancers. Acta Crystallogr D Biol Crystallogr 55, 1487-1489.

Alison M, Sarraf C. (1998) Hepatic stem cells. J. Hepat 29, 676-682.

Akhurst B., Croager E J, Farley-Roche C A, Ong. J K., Dumble M L, Knight B, Yeoh G C. (2001). A modified choline-deficient, ethionine-supplemented diet protocol effectively induces oval cells in mouse liver. Hepatology 34, 519-522.

Bedda S, Laurent A, Conti F, Chereau C, Tran A, Tran-Van Nhieu J, Jaffray P, Soubrane O, Goulvestre C, Calmus Y, Weill B, Batteux F. (2003) Mangafodipir prevents liver injury induced by acetaminophen in the mouse. J. Hepatol. November; 39 (5):765-72.

Christa, L., Felin, M., Morali, O., et al. (1994) The human HIP gene, overexpressed in primary liver cancer encodes for a C-Type carbohydrate binding protein with lactose binding activity. FEBS Letters 337, pp 114-118.

Christa, L., Carnot, F., Simon, M. T., Levasseur, F., Stinnakre; M. G., Lasserre, C., Thépot, D., Clément, B., Devinoy, E., Bréchot, C. (1996) HIP/PAP, a human C-type lectin, is an adhesive molecule expressed in hepatocellular carcinoma, as well as in normal paneth and pancreatic cells. Am. J. Physiol. 271, G993 G1002.

Christa L, Simon M T, Brezault-Bonnet C, Bonte E, Carnot F, Zylberberg H, Franco D, Capron F, Roskams T, Brechot C. (1999) Hepatocarcinoma-intestine-pancreas/pancreatic associated protein (HIP/PAP) is expressed and secreted by proliferating ductules as well as by hepatocarcinoma and cholangiocarcinoma cells. Am J Pathol 155, 1525-33.

Christa L. Pauloin A, Simon M T, Stinnakre M G, Fontaine M L, Delpal S. Ollivier-Bousquet M, Brechot C, Devinoy E. ((2000)) High expression of the human hepatocarcinoma-intestine-pancreas/pancreatic associated protein (HIP/PAP) gene in the mammary gland of lactating transgenic mice. Secretion into the milk and purification of the HIP/PAP lectin. Eur J. Biochem 267, 1665-1671.

Drickamer K. (1993) Calcium-dependent carbohydrate-recognition domains in animal proteins. Current Opinion in Structural Biology 3, 393-400.

Factor V M, Radaeva S A, Thorgeirsson S S. (1994) Origin and fate of oval cells in Dipin-induced hepatocarcinogenesis in the mouse. Am. J. Pathol. 145, 409-422.

Fausto N F. (1994) Liver stem cells. In: Arias I M, Boyer J L, Fausto N F, Jakoby W B, Schachter D A, Shafritz D A, editors. The liver: Biology and pathobiology. Third Ed. New York: Raven, 1501-1518.

Fausto N F. (2000) Liver regeneration. Journal of Hepatol 32:19-31.

Ferret P J, Hammoud R, Tulliez M, Tran A, Trebeden H, Jaffray P, Malassagne B, Calmus Y, Weill B, Batteux F. (2001) Detoxification of reactive oxygen species by a nonpeptidyl mimic of superoxide dismutase cures acetaminophen-induced acute liver failure in the mouse. Hepatology. May; 33 (5):1173-80.

Fu X X, Su C Y, Lee Y, Hintz R, Biempica L, Snyder R, Rogler C E (1988). Insulin like growth factor II expression and oval cell proliferation associated with hepatocarcinogenesis in woodchuck virus carriers. J. Virol. 62, 3422-3430.

Gang-Hong L, Merlino, G, Fautso, N, (1992) Development of liver tumors in transforming Growth Factor α transgenic mice. Cancer Research. 52, pp 5162-5170.

Heaton N (2003) Small-for-size liver syndrome after auxiliary and split liver transplantation: donor selection. Liver Transpl. 2003 September; 9 (9): S26-8.

Higgins G & Anderson R. (1931) Experimental pathology of the liver. Restoration of the liver of the white rat following partial surgical removal. Arch Pathol 12, 186-202.

Horigushi N, Takayama H, et al. (2002) Hepatocyte Growth Factor promotes hepatocarcinogenesis through c-Met autocrine activation and enhanced angiogenesis in transgenic mice treated with diethylnitrosamine. Oncogene 21, pp 1791-1799.

Klaunig J E, Goldblatt P J, Hinton D E, Lipsky M M, Chacko J. Trump B F (1981) Mouse liver cell culture. I. Hepatocyte isolation. In vitro 10, 913-925.

Kreamer B L, Staecker J L, Sawada N, Sattler G L, Hsia M T, Pitot H C (1986) Use of a low-speed, iso-density percoll centrifugation method to increase the viability of isolated rat hepatocyte preparations. In vitro Cell Dev Biol 4, 201-211.

Laemmli, U. K. (1970) Cleavage of structural proteins during the assembly of the head of bacteriophage T4. Nature (London) 227, 680 685.

Lasserre, C., Christa, L., Simon, M. T., Vernier, P., Bréchot, C. (1992) A novel gene (HIP) activated in human primary liver cancer. Cancer Res. 52, 5089 5095.

Lee G H, Merlino G, Fausto N. (1992) Development of liver tumors in transforming growth factor alpha transgenic mice. Cancer Res, October 1; 52 (19): 5162-70.

Leist M, Gantner F, Bohlinger I, Germann P G, Tiegs G, Wendel A. (1994) Murine hepatocyte apoptosis induced in vitro and in vivo by TNF-alpha requires transcriptional arrest. J. Immunol 15, 1778-1788.

Libbrecht L, De Vos R, Cassiman D, Desmet V, Aerts R, Roskams T. (2001) Hepatic progenitor cells in hepatocellular adenomas. Am J Surg Pathol 11, 1388-96.

Mitchell Claudia and Fausto Nelson (2002) Bone Marrow-derived hepatocytes rare but promising Am. J. Pathol, vol 161, 349-350

Orelle, B., Keim, V., Masciotra, L., Dagorn, J. C., and Iovanna, J. L. (1992) J. Clin. Invest 90, 2284-2291.

Petersen B E, Zajac V F, Michalopoulos G K. (1998) Hepatic oval cell activation in response to injury following chemically induced periportal or pericentral damage in rats. Hepatology 27, 1030-1038.

Petersen B E, Bowen W. C. et al. (1999) Bone marrow as a potential source of hepatic oval cells. Science vol 284, 1168-1170

Peterson, G. L. (1977) A simplification of the protein assay method of Lowry et al. which is more generally applicable. *Anal. Biochem.* 83, 346 356.

Pinkert C A, Ornitz D M, Brinster R L, Palmiter R D (1987) An albumin enhancer located 10 kb upstream functions along with its promoter to direct efficient, liver-specific expression in transgenic mice. Genes Dev 3, 268-276.

Renton K W, Deloria L B, Mannering G J (1978) Effects of polyribonoinosinic acid polyribocytidylic acid and a mouse interferon preparation on cytochrome P-450-dependent monooxygenase systems in cultures of primary mouse hepatocytes. Mol. Pharmacol 4, 672-681.

Roskams T, De Vos R, Van Eyken P, Myazaki H, Van Damme B, Desmet V. (1198). Hepatic OV-6 expression in human liver disease and rat experiments: evidence for hepatic progenitor cells in man. J. Hepatol 29, 455-463.

Sell S. (1998) Comparison of liver progenitor cells in human atypical ductular reactions with those seen in experimental models of liver injury. Hepatology 27, 317-331.

Simon M T, Pauloin A, Normand G, Lieu H T, Mouly H, Pivert G, Carnot F, Tralhao J G, Brechot C, Christa L. (2003) HIP/PAP stimulates liver regeneration after partial hepatectomy and combines mitogenic and anti-apoptotic functions through the PKA signaling pathway. FASEB J. 17 (11) 1441-50.

Sirica A E, Gainey T W, Harrel M B, Caran N. (1997) Cholangiocarcinogenesis and biliary adaptation responses in hepatic injury. In: Biliary and pancreatic ductal epithelia; Pathobiology and Pathophysiology. Edited by Sirica A E, Longnecker D S. New York, Marcel Dekker, 229-290.

Terradillos O, Billet O, Renard C A, Levy R, Molina T, Briand P, Buendia M A. (1997) The hepatitis B virus X gene potentiates c-myc-induced liver oncogenesis in transgenic mice. Oncogene. January 30; 14 (4):395-404.

Thépot, D., Devinoy, E., Fontaine, M. L., Stinnakre, M. G., Massoud, M., Kann, G., Houdebine, L. M. (1995) Rabbit whey acidic protein gene upstream region controls high-level expression of bovine growth hormone in the mammary gland of transgenic mice. *Mol. Reprod. Dev.* 42, 261 267.

Tralhao J G, Roudier J, Morosan S, Giannini C, Tu H, Goulenok C, Carnot F, Zavala F, Joulin V, Kremsdorf D, Brechot C. (2002) Paracrine in vivo inhibitory effects of hepatitis B virus X protein (HBx) on liver cell proliferation: an alternative mechanism of HBx-related pathogenesis. Proc Natl Acad Sci USA. May 14; 99 (10):6991-6.

The invention claimed is:

1. A method of stimulating liver regeneration in vivo, protecting against liver failure, or protecting against apoptosis of hepatocytes in a subject comprising:
   obtaining a pharmaceutical composition comprising a polypeptide comprising an amino acid sequence having at least 90% amino acid identity with an amino acid sequence from amino acid residue 27 to amino acid residue 175 of SEQ ID NO:1; and
   administering the pharmaceutical composition to a subject, thereby stimulating liver regeneration in vivo, protecting against liver failure, or protecting against apoptosis of hepatocytes, wherein said subject has liver failure, liver necrosis, a liver disease, a partial liver transplant, hepatic cirrhosis, or a hepatic cancer, or wherein said subject has had a liver resection.

2. The method of claim 1, wherein the polypeptide is further defined as comprising an amino acid sequence having at least 90% amino acid identity with the amino acid sequence of SEQ ID NO:1.

3. The method of claim 1, wherein the polypeptide is further defined as comprising an amino acid sequence from amino acid residue 36 to amino acid residue 175 of SEQ ID NO:1.

4. The method of claim 3, wherein the polypeptide is further defined as comprising the amino acid sequence from amino acid residue 27 to amino acid residue 175 of SEQ ID NO:1.

5. The method of claim 1, wherein the polypeptide is further defined as a human hepatocarcinoma-intestine-pancreas/pancreatic-associated protein (HIP/PAP) with the amino acid sequence of SEQ ID NO:1.

6. The method of claim 1, wherein the subject is a human.

7. The method of claim 1, wherein the subject has chronic or acute liver failure.

8. The method of claim 1, wherein the subject has liver necrosis.

9. The method of claim 1, wherein the subject has had a liver resection.

10. The method of claim 1, wherein the subject has a partial liver transplant or hepatic cirrhosis.

11. The method of claim 10, wherein the subject has hepatic cirrhosis of alcoholic, viral, or drug cause.

12. The method of claim 1, wherein the subject has liver failure caused by a disorder selected from the group consisting of Hepatitis B, Hepatitis C, Urea Cycle defects, Familial hypercholesterolemia, Alcohol induced cirrhosis, Glycogen Storage Disease, Autoimmune Hepatitis, Primary Hyperoxaluria type 1, Cryptogenic cirrhosis, Crigler-Najjar syndrome type 1, Congenital Hepatic Fibrosis, Niemann-Pick Disease, Primary Biliary Cirrhosis, Familial Amyloidosis, Biliary Atresia, Hepatocellular Carcinoma, Primary Sclerosing Cholangitis, Hepatoblastoma, Alagille Syndrome, Hemangioendothelioma, Familial Cholestasis, Non-Carcinoid neuroendocrine tumor, Drug induced liver failure, benign liver tumor, liver tumor, Acute liver failure, Budd-Chiari syndrome, Alpha-1-antitrypsin deficiency, Wilson Disease, Hemochromatosis, Tyrosinemia, Protoporphyria, cystic fibrosis, steatosis, non-alcoholic statohepatitis (NASH), and non-alcoholic fatty liver disease (NAFLD).

13. The method of claim 1, wherein the pharmaceutical composition further comprises a therapeutically effective amount of a hepatotoxic compound.

14. The method of claim 1, wherein the subject has a liver disease.

15. The method of claim 1, wherein the subject has liver failure.

16. The method of claim 15, wherein the liver failure is caused by liver disease.

17. The method of claim 15, wherein the liver failure is caused by a liver resection, a liver transplantation, a viral infection, alcohol, or drug poisoning.

18. The method of claim 1, wherein the subject has a hepatic cancer.

19. The method of claim 18, wherein the hepatic cancer is a primary liver tumor or a metastatic liver tumor.

20. The method of claim 12, wherein the subject has Drug induced liver failure.

* * * * *

SEQUENCE LISTING

```
<160> NUMBER OF SEQ ID NOS: 1

<210> SEQ ID NO 1
<211> LENGTH: 175
<212> TYPE: PRT
<213> ORGANISM: Homo sapiens

<400> SEQUENCE: 1

Met Leu Pro Pro Met Ala Leu Pro Ser Val Ser Trp Met Leu Leu Ser
  1               5                  10                  15

Cys Leu Met Leu Leu Ser Gln Val Gln Gly Glu Glu Pro Gln Arg Glu
                 20                  25                  30

Leu Pro Ser Ala Arg Ile Arg Cys Pro Lys Gly Ser Lys Ala Tyr Gly
             35                  40                  45

Ser His Cys Tyr Ala Leu Phe Leu Ser Pro Lys Ser Trp Thr Asp Ala
         50                  55                  60

Asp Leu Ala Cys Gln Lys Arg Pro Ser Gly Asn Leu Val Ser Val Leu
 65                  70                  75                  80

Ser Gly Ala Glu Gly Ser Phe Val Ser Ser Leu Val Lys Ser Ile Gly
                 85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175
```